US006313138B1

(12) United States Patent
Fraley et al.

(10) Patent No.: US 6,313,138 B1
(45) Date of Patent: Nov. 6, 2001

(54) TYROSINE KINASE INHIBITORS

(75) Inventors: Mark E. Fraley, North Wales; George D. Hartman, Lansdale, both of PA (US); Randall W. Hartman, Newbury Park, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/788,720

(22) Filed: Feb. 20, 2001

Related U.S. Application Data
(60) Provisional application No. 60/185,024, filed on Feb. 25, 2000.

(51) Int. Cl.[7] ............... A61K 31/435; C07D 471/04; C07D 491/048; C07D 495/04
(52) U.S. Cl. ............... 514/300; 514/301; 514/302; 546/113; 546/114; 546/116
(58) Field of Search ................... 546/113, 114, 546/116; 514/300, 301, 302

(56) References Cited

U.S. PATENT DOCUMENTS
5,409,930  4/1995  Spada et al. .

FOREIGN PATENT DOCUMENTS
| | | |
|---|---|---|
| WO 92/20642 | 11/1992 | (WO) . |
| WO 97/06144 | 2/1997 | (WO) . |
| WO 97/19927 | 6/1997 | (WO) . |
| WO 97/44037 | 11/1997 | (WO) . |
| WO 98/23613 | 6/1998 | (WO) . |
| WO 00/09495 | 2/2000 | (WO) . |

OTHER PUBLICATIONS
Chinese Science Bulletin, vol. 36, No. 24, pp. 2056–2060 (1991), by Meng, et al.
Science in China (Series B), vol. 36, No. 5, pp 540–549, by Meng, et al.
Oncogene, vol. 6, pp. 1677–1683 (1991), by Terman, et al.
J. of Clin. Invest., vol. 104, No. 11, pp. 1613–1620 (1999), by van Bruggen, et al.
Drug News Perspect, vol. No. 5, pp. 265–270 (1998), by D. A. Greenberg.
Nature, vol. 407, pp. 242–248 (2000), by Yancopoulos, et al.
Nature, vol. 407, pp. 249–257 (2000), by Carmeliet, et al.
J. Heterocyclic Chem., vol. 28, pp. 1481–1484 (1991), by Meng, et al.
Nature Biotech., vol. 17, pp. 963–968 (1999), by V. Brower.
Nature Medicine, vol. 5, No. 6, pp. 623–628, by Gerber, et al.
Molecular Cell, vol. 4, pp. 915–924 (1999), by Eliceiri, et al.
Stem Cells, vol. 12, pp. 1–6 (1994), by T.R. Burke, Jr.
Platelets, vol. 10, pp. 285–292 (1999), by Amirkhosravi, et al.
FEBS Letters, vol. 473, pp. 161–164 (2000), by Nakagawa, et al.
Endocrinology, Abstract, vol. 141, No. 5, by Deckers, et al.
Oncogene, vol. 5, pp. 519–524 (1990), by Shibuya, et al.
J. Med. Chem., vol. 37, pp. 2129–2137 (1994), by Maguire, et al.
J. Med. Chem., vol. 42, pp. 5369–5389 (1999), by Hennequin, et al.

*Primary Examiner*—Bernard Dentz
(74) *Attorney, Agent, or Firm*—J. Antonio Garcia-Rivas; Mark R. Daniel

(57) ABSTRACT

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

32 Claims, No Drawings

TYROSINE KINASE INHIBITORS

RELATED APPLICATIONS

This application claims priority under 35 U.S.C. §119(e) from U.S. Provisional Application No. 60/185,024, filed Feb. 25, 2000.

BACKGROUND OF THE INVENTION

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

Tyrosine kinases are a class of enzymes that catalyze the transfer of the terminal phosphate of adenosine triphosphate to tyrosine residues in protein substrates. Tyrosine kinases are believed, by way of substrate phosphorylation, to play critical roles in signal transduction for a number of cell functions. Though the exact mechanisms of signal transduction is still unclear, tyrosine kinases have been shown to be important contributing factors in cell proliferation, carcinogenesis and cell differentiation.

Tyrosine kinases can be categorized as receptor type or non-receptor type. Receptor type tyrosine kinases have an extracellular, a transmembrane, and an intracellular portion, while non-receptor type tyrosine kinases are wholly intracellular.

The receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR, HER2, HER3, and HER4. Ligands of this subfamily of receptors include epithileal growth factor, TGF-α, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-α and β receptors, CSFIR, c-kit and FLK-II. Then there is the FLK family which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., *DN&P* 7(6):334–339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen *Oncogene*, 8:2025–2031 (1993), which is hereby incorporated by reference.

Both receptor-type and non-receptor type tyrosine kinases are implicated in cellular signaling pathways leading to numerous pathogenic conditions, including cancer, psoriasis and hyperimmune responses.

Several receptor-type tyrosine kinases, and the growth factors that bind thereto, have been suggested to play a role in angiogenesis, although some may promote angiogenesis indirectly (Mustonen and Alitalo, *J. Cell Biol.* 129:895–898, 1995). One such receptor-type tyrsoine kinase is fetal liver kinase 1 or FLK-1. The human analog of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., *Onocogene* 8(1):11–15, 1993). VEGF and KDR are a ligand-receptor pair that play an important role in the proliferation of vascular endo-thelial cells, and the formation and sprouting of blood vessels, termed vasculogenesis and angiogenesis, respectively.

Angiogenesis is characterized by excessive activity of vascular endothelial growth factor (VEGF). VEGF is actually comprised of a family of ligands (Klagsburn and D'Amore, *Cytokine &Growth Factor Reviews* 7:259–270, 1996). VEGF binds the high affinity membrane-spanning tyrosine kinase receptor KDR and the related fms-like tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF whereas Flt-1 appears to modulate non-mitogenic functions such as those associated with cellular adhesion. Inhibiting KDR thus modulates the level of mitogenic VEGF activity. In fact, tumor growth has been shown to be susceptible to the antiangiogenic effects of VEGF receptor antagonists. (Kim et al., Nature 362, pp. 841–844, 1993).

Solid tumors can therefore be treated by tyrosine kinase inhibitors since these tumors depend on angiogenesis for the formation of the blood vessels necessary to support their growth. These solid tumors include histiocytic lymphoma, cancers of the brain, genitourinary tract, lymphatic system, stomach, larynx and lung, including lung adenocarcinoma and small cell lung cancer. Additional examples include cancers in which overexpression or activation of Raf-activating oncogenes (e.g., K-ras, erb-B) is observed. Such cancers include pancreatic and breast carcinoma. Accordingly, inhibitors of these tyrosine kinases are useful for the prevention and treatment of proliferative diseases dependent on these enzymes.

The angiogenic activity of VEGF is not limited to tumors. VEGF accounts for most of the angiogenic activity produced in or near the retina in diabetic retinopathy. This vascular growth in the retina leads to visual degeneration culminating in blindness. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf, src and mutant p53 (all of which are relevant to targeting cancer). Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells.

Viral expression of a VEGF-binding construct of Flk-1, Flt-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. Inhibition of KDR or Flt-1 is implicated in pathological angiogenesis, and these receptors are useful in the treatment of diseases in which angiogenesis is part of the overall pathology, e.g., inflammation, diabetic retinal vascularization, as well as various forms of cancer since tumor growth is known to be dependent on angiogenesis. (Weidner et al., N. Engl. J. Med., 324, pp. 1–8, 1991).

Accordingly, the identification of small compounds which specifically inhibit, regulate and/or modulate the signal transduction of tyrosine kinases is desirable and is an object of this invention.

SUMMARY OF THE INVENTION

The present invention relates to compounds that are capable of inhibiting, modulating and/or regulating signal transduction of both receptor-type and non-receptor type tyrosine kinases. One embodiment of the present invention is illustrated by a compound of Formula I, and the pharmaceutically acceptable salts and stereoisomers thereof:

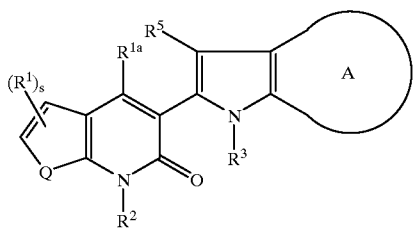

I

DETAILED DESCRIPTION OF THE INVENTION

The compounds of this invention are useful in the inhibition of kinases and are illustrated by a compound of Formula I:

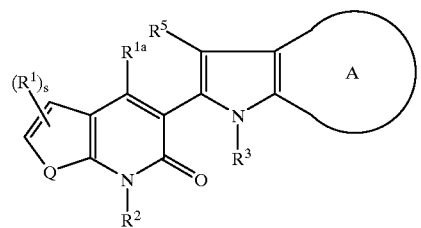

I or a pharmaceutically acceptable salt or stereoisomer thereof, wherein

Q is S, O, or —E=D—;

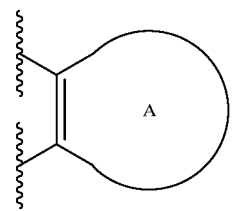

is selected from the following:

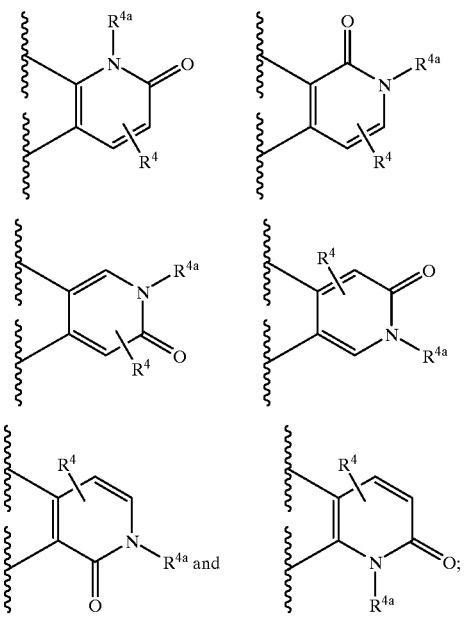

a is 0 or 1;
b is 0 or 1;
s is 1 or 2;
m is 0, 1, or 2;
E=D is C=N, N=C, or C=C;
$R^1$, $R^{1a}$, $R^4$ and $R^5$ are independently selected from:
1) H,
2) $(C=O)_a O_b C_1$–$C_{10}$ alkyl, optionally substituted with one to three substituents selected from $R^6$,
3) $(C=O)_a O_b$ aryl, optionally substituted with one to three substituents selected from $R^6$,
4) $(C=O)_a O_b C_2$–$C_{10}$ alkenyl, optionally substituted with one to three substituents selected from $R^6$,
5) $(C=O)_a O_b C_2$–$C_{10}$ alkynyl, optionally substituted with one to three substituents selected from $R^6$, 6) $SO_mC_1-C_{10}$ alkyl, optionally substituted with one to three substituents selected from $R^6$,
7) $SO_m$aryl, optionally substituted with one to three substituents selected from $R^6$,
8) $CO_2H$,
9) halo,
10) CN,
11) OH,
12) $O_bC_1-C_6$ perfluoroalkyl, and
13) $(C=O)_aNR^7R^8$;

$R^2$ and $R^3$ are independently selected from the group consisting of:
1) H,
2) $(C=O)O_aC_1-C_{10}$ alkyl,
3) $(C=O)O_a$aryl,
4) $C_1-C_{10}$ alkyl,
5) $SO_mC_1-C_{10}$ alkyl,
6) $SO_m$aryl,
7) $(C=O)_aO_bC_2-C_{10}$ alkenyl,
8) $(C=O)_aO_bC_2-C_{10}$ alkynyl, and
9) aryl, said alkyl, aryl, alkenyl and alkynyl is optionally substituted with one to three substituents selected from $R^6$;

$R^{4a}$ is selected from the group consisting of:
1) $(C=O)O_aC_1-C_{10}$ alkyl,
2) $(C=O)O_a$aryl,
3) $C_1-C_{10}$ alkyl,
4) $SO_mC_1-C_{10}$ alkyl,
5) $SO_m$aryl,
6) $(C=O)_aO_bC_2-C_{10}$ alkenyl,
7) $(C=O)_aO_bC_2-C_{10}$ alkynyl, and
8) aryl, said alkyl, aryl, alkenyl and alkynyl is optionally substituted with one to three substituents selected from $R^6$;

$R^6$ is:
1) H,
2) $(C=O)_aO_bC_1-C_6$ alkyl,
3) $(C=O)_aO_b$aryl, optionally substituted with one to three substituents selected from $R^{6a}$,
4) $C_2-C_{10}$ alkenyl,
5) $C_2-C_{10}$ alkynyl,
6) heterocyclyl, optionally substituted with one to three substituents selected from $R^{6a}$,
7) $CO_2H$,
8) halo,
9) CN,
10) OH,
11) oxo,
12) $O_bC_1-C_6$ perfluoroalkyl, or
13) $NR^7R^8$;

$R^{6a}$ is:
1) H,
2) $SO_m$aryl,
3) $SO_mC_1-C_6$ alkyl,
4) $(C=O)_aO_bC_1-C_6$ alkyl,
5) $(C=O)_aO_b$aryl,
6) $C_2-C_{10}$ alkenyl,
7) $C_2-C_{10}$ alkynyl,
8) heterocyclyl,
9) $CO_2H$,
10) halo,
11) CN,
12) OH,
13) oxo,
14) $O_bC_1-C_6$ perfluoroalkyl, or
15) $N(C_1-C_6 \text{ alkyl})_2$;

$R^7$ and $R^8$ are independently selected from:
1) H,
2) $(C=O)O_bC_1-C_{10}$ alkyl, optionally substituted with one to three substituents selected from $R^{6a}$,
3) $(C=O)O_b$aryl, optionally substituted with one to three substituents selected from $R^{6a}$,
4) $C_1-C_{10}$ alkyl, optionally substituted with one to three substituents selected from $R^{6a}$,
5) aryl, optionally substituted with one to three substituents selected from $R^{6a}$,
6) $C_2-C_{10}$ alkenyl, optionally substituted with one to three substituents selected from $R^{6a}$,
7) $C_2-C_{10}$ alkynyl, optionally substituted with one to three substituents selected from $R^{6a}$, and
8) heterocyclyl, or $R^7$ and $R^8$ can be taken together with the nitrogen to which they are attached to form a 5–7 membered heterocycle containing, in addition to the nitrogen, one or two additional heteroatoms selected from N, O and S, said heterocycle optionally substituted with one to three substituents selected from $R^{6a}$.

A second embodiment is illustrated by the compound of Formula I, as described above, wherein Q is E=D. In a third embodiment, E=D is further defined as C=C.

A fourth embodiment of the invention is the compound of Formula I, as described above, wherein Q is E=D; E=D is C=C;

$R^1$, $R^{1a}$, $R^4$ and $R^5$ are independently selected from:
1) H,
2) $(C=O)_aO_bC_1-C_6$ alkyl, optionally substituted with one to three substituents selected from $R^6$,
3) $(C=O)_aO_b$aryl, optionally substituted with one to three substituents selected from $R^6$,
4) $(C=O)_aO_bC_2-C_6$ alkenyl, optionally substituted with one to three substituents selected from $R^6$,
5) $CO_2H$,
6) halo,
7) CN,
8) OH,
9) $O_bC_1-C_3$ perfluoroalkyl, and
10) $(C=O)_aNR^7R^8$;

$R^2$ and $R^3$ are independently selected from the group consisting of:
1) H,
2) $(C=O)O_aC_1-C_6$ alkyl, and
3) $C_1-C_6$ alkyl;

$R^{4a}$ is $(C=O)O_aC_1-C_6$ alkyl or $C_1-C_6$ alkyl;

$R^6$ is:
1) H,
2) $(C=O)_aO_bC_1-C_6$ alkyl,
3) $(C=O)_aO_b$aryl, optionally substituted with one to three substituents selected from $R^{6a}$,
4) $C_2-C_6$ alkenyl,
5) heterocyclyl, optionally substituted with one to three substituents selected from $R^{6a}$,
6) $CO_2H$,
7) halo,
8) CN,
9) OH,
10) oxo,
11) $O_bC_1-C_3$ perfluoroalkyl, or
12) $NR^7R^8$;

$R^{6a}$ is:
1) H,
2) $SO_m$aryl,
3) $SO_mC_1-C_6$ alkyl,
4) $(C=O)_aO_bC_1-C_6$ alkyl, 5) (C=O)$_a$O$_b$aryl,
6) $C_2$-$C_6$ alkenyl,
7) heterocyclyl,
8) $CO_2H$,
9) halo,
10) CN,
11) OH,
12) oxo,
13) O$_b$C$_1$-C$_3$ perfluoroalkyl, or
14) N(C$_1$-C$_6$ alkyl)$_2$;

$R^7$ and $R^8$ are independently selected from:
1) H,
2) (C=O)O$_b$C$_1$-C$_6$ alkyl, optionally substituted with one to three substituents selected from $R^{6a}$,
3) (C=O)O$_b$aryl, optionally substituted with one to three substituents selected from $R^{6a}$,
4) $C_1$-$C_6$ alkyl, optionally substituted with one to three substituents selected from $R^{6a}$,
5) aryl, optionally substituted with one to three substituents selected from $R^{6a}$,
6) $C_2$-$C_6$ alkenyl, optionally substituted with one to three substituents selected from $R^{6a}$, and
7) heterocyclyl, or $R^7$ and $R^8$ can be taken together with the nitrogen to which they are attached to form a 5–7 membered heterocycle containing, in addition to the nitrogen, one or two additional heteroatoms selected from N, O and S, said heterocycle optionally substituted with one to three substituents selected from $R^{6a}$.

In a fifth embodiment of the invention, the compound of Formula I is defined such that Q is E=D; E=D is C=C;
a is 0 or 1;
b is 0 or 1;
s is 1;

$R^1$ and $R^4$ are independently selected from:
1) H,
2) (C=O)$_a$O$_b$C$_1$-C$_6$ alkyl, optionally substituted with one to three substituents selected from $R^6$,
3) (C=O)$_a$O$_b$aryl, optionally substituted with one to three substituents selected from $R^6$,
4) (C=O)$_a$O$_b$C$_2$-C$_6$ alkenyl, optionally substituted with one to three substituents selected from $R^6$,
5) (C=O)$_a$O$_b$C$_2$-C$_6$ alkynyl, optionally substituted with one to three substituents selected from $R^6$,
6) $CO_2H$,
7) halo,
8) CN,
9) OH,
10) O$_b$C$_1$-C$_3$ perfluoroalkyl, and
11) (C=O)$_a$NR$^7$R$^8$;

$R^2$ and $R^3$ are independently selected from H and methyl;
$R^{4a}$ is methyl;
$R^5$ and $R^{1a}$ are H;
$R^6$ is:
1) H,
2) (C=O)$_a$O$_b$C$_1$-C$_6$ alkyl,
3) (C=O)$_a$O$_b$aryl, optionally substituted with one to three substituents selected from $R^{6a}$,
4) $C_2$-$C_{10}$ alkenyl,
5) $C_2$-$C_{10}$ alkynyl,
6) heterocyclyl, optionally substituted with one to three substituents selected from $R^{6a}$,
7) $CO_2H$,
8) halo,
9) CN,
10) OH,
11) oxo,
12) O$_b$C$_1$-C$_3$ perfluoroalkyl, or
13) NR$^7$R$^8$;

$R^{6a}$ is:
1) H,
2) SO$_m$aryl,
3) SO$_m$C$_1$-C$_6$ alkyl,
4) (C=O)$_a$O$_b$C$_1$-C$_6$ alkyl,
5) (C=O)$_a$O$_b$aryl,
6) $C_2$-$C_{10}$ alkenyl,
7) $C_2$-$C_{10}$ alkynyl,
8) heterocyclyl,
9) $CO_2H$,
10) halo,
11) CN,
12) OH,
13) oxo,
14) O$_b$C$_1$-C$_3$ perfluoroalkyl, or
15) N(C$_1$-C$_6$ alkyl)$_2$;

$R^7$ and $R^8$ are independently selected from:
1) H,
2) (C=O)O$_b$C$_1$-C$_6$ alkyl, optionally substituted with one to three substituents selected from $R^{6a}$,
3) (C=O)O$_b$aryl, optionally substituted with one to three substituents selected from $R^{6a}$,
4) $C_1$-$C_{10}$ alkyl, optionally substituted with one to three substituents selected from $R^{6a}$,
5) aryl, optionally substituted with one to three substituents selected from $R^{6a}$,
6) $C_2$-$C_6$ alkenyl, optionally substituted with one to three substituents selected from $R^{6a}$,
7) $C_2$-$C_6$ alkynyl, optionally substituted with one to three substituents selected from $R^{6a}$, and
8) heterocyclyl, or $R^7$ and $R^8$ can be taken together with the nitrogen to which they are attached to form a piperidinyl, piperazinyl, morpholinyl or pyrrolidinyl group, optionally substituted with one or two substituents selected from $R^{6a}$.

Yet another embodiment of the present invention is a compound which is 3-(4-methyl-5-oxo-4,5-dihydro-1H-pyrrolo[3,2-b]pyridin-2-yl)-1H-quinolin-2-one or a pharmaceutically acceptable salt or stereoisomer thereof.

Also included within the scope of the present invention is a pharmaceutical composition which is comprised of a compound of Formula I as described above and a pharmaceutically acceptable carrier. The present invention also encompasses a method of treating or preventing cancer in a mammal in need of such treatment which is comprised of administering to said mammal a therapeutically effective amount of a compound of Formula I. Preferred cancers for treatment are selected from cancers of the brain, genitourinary tract, lymphatic system, stomach, larynx and lung. Another set of preferred forms of cancer are histiocytic lymphoma, lung adenocarcinoma, small cell lung cancers, pancreatic cancer, gioblastomas and breast carcinoma.

Also included is a method of treating or preventing a disease in which angiogenesis is implicated, which is comprised of administering to a mammal in need of such treatment a therapeutically effective amount of a compound of Formula I. Such a disease in which angiogenesis is implicated is ocular diseases such as retinal vascularization, diabetic retinopathy, age-related macular degeneration, and the like.

Also included within the scope of the present invention is a method of treating or preventing inflammatory diseases which comprises administering to a mammal in need of such treatment a therapeutically effective amount of a compound of Formula I. Examples of such inflammatory diseases are rheumatoid arthritis, psoriasis, contact dermatitis, delayed hypersensitivity reactions, and the like.

Also included is a method of treating or preventing a tyrosine kinase-dependent disease or condition in a mammal which comprises administering to a mammalian patient in need of such treatment a therapeutically effective amount of a compound of Formula I. The therapeutic amount varies according to the specific disease and is discernable to the skilled artisan without undue experimentation.

A method of treating or preventing retinal vascularization which is comprised of administering to a mammal in need of such treatment a therapeutically effective amount of compound of Formula I is also encompassed by the present invention. Methods of treating or preventing ocular diseases, such as diabetic retinopathy and age-related macular degeneration, are also part of the invention. Also included within the scope of the present invention is a method of treating or preventing inflammatory diseases, such as rheumatoid arthritis, psoriasis, contact dermatitis and delayed hypersensitivity reactions, as well as treatment or prevention of bone associated pathologies selected from osteosarcoma, osteoarthritis, and rickets.

The invention also contemplates the use of the instantly claimed compounds in combination with a second compound selected from:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

Preferred angiogenesis inhibitors are selected from the group consisting of a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, and an antibody to VEGF. Preferred estrogen receptor modulators are tamoxifen and raloxifene.

Also included in the scope of the claims is a method of treating cancer which comprises administering a therapeutically effective amount of a compound of Formula I in combination with radiation therapy and/or in combination with a compound selected from:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

And yet another embodiment of the invention is a method of treating cancer which comprises administering a therapeutically effective amount of a compound of Formula I in combination with paclitaxel or trastuzumab.

Also within the scope of the invention is a method of reducing or preventing tissue damage following a cerebral ischemic event which comprises administering a therapeutically effective amount of a compound of Formula I.

Another embodiment of the invention is a method of treating or preventing cancer which comprises administering a therapeutically effective amount of a compound of Formula I in combination with a COX-2 inhibitor.

These and other aspects of the invention will be apparent from the teachings contained herein.

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include the proliferation of tumor cells, the pathologic neovascularization that supports solid tumor growth, ocular neovascularization (diabetic retinopathy, age-related macular degeneration, and the like) and inflammation (psoriasis, rheumatoid arthritis, and the like).

The compounds of the present invention may have asymmetric centers, chiral axes, and chiral planes (as described in: E. L. Eliel and S. H. Wilen, *Stereo-chemistry of Carbon Carbon Compounds,* John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

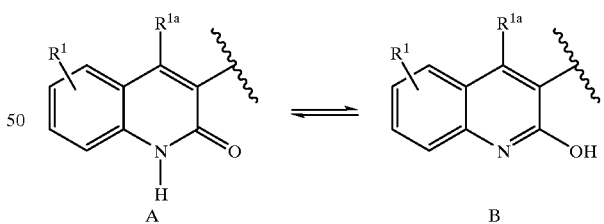

When any variable (e.g. aryl, heterocycle, $R^1$, $R^2$ etc.) occurs more than one time in any constituent, its definition on each occurrence is independent at every other occurrence. Also, combinations of substituents and variables are permissible only if such combinations result in stable compounds. Lines drawn into the ring systems from substituents (such as from $R^1$, $R^2$, $R^3$, $R^4$ etc.) indicate that the indicated bond may be attached to any of the substitutable ring carbon atoms. If the ring system is polycyclic, it is intended that the bond be attached to any of the suitable carbon atoms on the proximal ring only. For example,

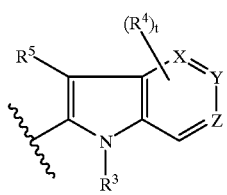

can be, inter alia, any of the following when:
X and Z are C,
Y is N,
$R^5$ is $CH_3$,
$R^3$ is H, and
$(R^4)_t$ is as defined in the claims:

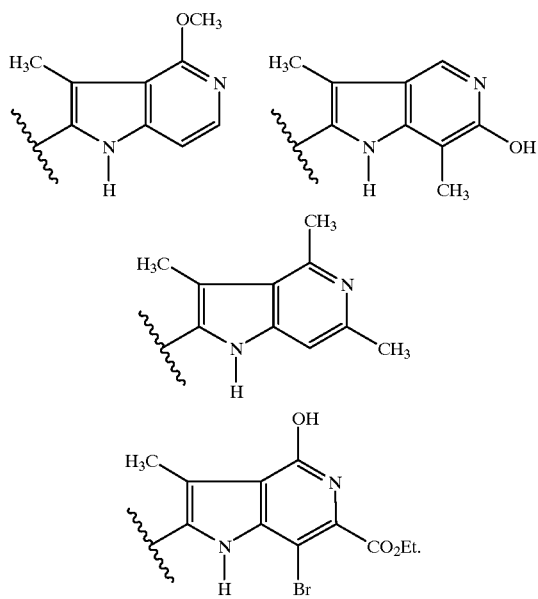

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

As used herein, "alkyl" is intended to include both branched, straight-chain, and cyclic saturated aliphatic hydrocarbon groups having the specified number of carbon atoms. For example, $C_1$–$C_{10}$, as in "$C_1$–$C_{10}$ alkyl" is defined to include groups having 1, 2, 3, 4, 5, 6, 7, 8, 9 or 10 carbons in a linear, branched, or cyclic arrangement. For example, "$C_1$–$C_{10}$ alkyl" specifically includes methyl, ethyl, propyl, butyl, pentyl, hexyl, heptyl, octyl, nonyl, decyl, and so on, as well as cycloalkyls such as cyclopropyl, cyclobutyl, cyclopentyl, cyclohexyl, tetrahydronaphthalene, methylenecylohexyl, and so on. "Alkoxy" represents an alkyl group of indicated number of carbon atoms attached through an oxygen bridge.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to 4 non-aromatic carbon-carbon double bonds may be present. Thus, "$C_2$–$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to 3 carbon-carbon triple bonds may be present. Thus, "$C_2$–$C_6$ alkynyl" means an alkynyl radical having from 2 to 6 carbon atoms. Alkynyl groups include ethynyl, propynyl and butynyl. As described above with respect to alkyl, the straight, branched or cyclic portion of the alkynyl group may contain triple bonds and may be substituted if a substituted alkynyl group is indicated.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. In cases where the heteroaryl substituent is bicyclic and one ring is non-aromatic or contains no heteroatoms, it is understood that attachment is via the aromatic ring or via the heteroatom containing ring, respectively.

As appreciated by those of skill in the art, "halo" or "halogen" as used herein is intended to include chloro, fluoro, bromo and iodo. The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

In certain instances, $R^7$ and $R^8$ are defined such that they can be taken together with the nitrogen to which they are attached to form a 5–7 membered heterocycle containing, in addition to the nitrogen, one or two additional heteroatoms selected from N, O and S, said heterocycle optionally substituted with one to three substituents selected from $R^{6a}$. Examples of the 5–7 membered ring systems that can thus be formed include, but are not limited to the following:

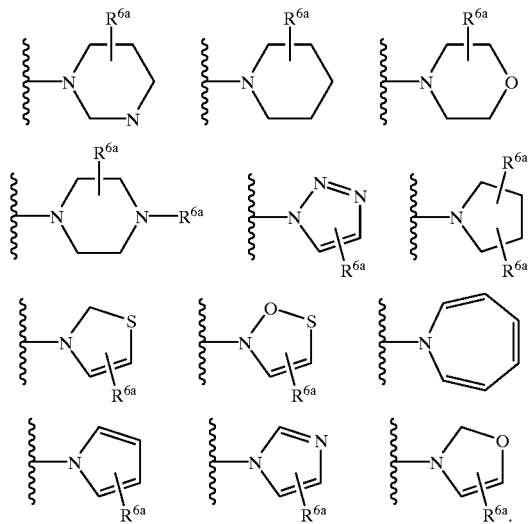

Preferably Q is E=D and E=D is C=C.
Preferably $R^1$ is H, $C_1$–$C_6$ alkyl, or aryl. Most preferably $R^1$ is H or $C_1$–$C_6$ alkyl.
The preferred definition of $R^{1a}$ is H.

Preferably $R^2$ and $R^3$ are independently H, $C_1$–$C_6$ alkyl, or (C=O)$C_1$–$C_6$ alkyl. Most preferably $R^2$ and $R^3$ are independently H or $C_1$–$C_6$ alkyl.
Preferably $R^4$ is OH, O$C_1$–$C_6$ alkyl, $C_1$–$C_6$ alkyl.
Preferably $R^{4a}$ is $C_1$–$C_6$ alkyl.
Preferably $R^5$ is H or $C_1$–$C_6$ alkyl. Most preferably $R^5$ is H.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The compounds of this invention may be prepared by employing reactions as shown in the following schemes, in addition to other standard manipulations that are known in the literature or exemplified in the experimental procedures. These schemes, therefore, are not limited by the compounds listed nor by any particular substituents employed for illustrative purposes. Substituent numbering as shown in the schemes does not necessarily correlate to that used in the claims.

Synopsis of Schemes

As shown in Scheme 1, the quinoline reagent 1-2 can be synthesized by the general procedures taught in Marsais, F; Godard, A.; Queguiner, G. *J. Hetero-cyclic Chem.* 1989, 26, 1589–1594). Derivatives with varying substitution can be made by modifying this procedure and use of standard synthetic protocols known in the art. Intermediate 1-2 is then coupled with the appropriate N-protected pyrollo-compound, structure 1-4, to produce a chlorinated intermediate of structure 1-5. At least one of the R4 substituents would be OH or OR on the carbon adjacent to the ring nitrogen. Heating of 1-5 in aqueous acetic acid produces the desired de-chlorinated product, 1-6. Scheme 2 shows an example using this route to arrive at a [3,2]-pyridno-pyrole, 2-3.

As shown in Scheme 3, the α-alkyloxy pyridino-pyroles 3-1 can be converted to the corresponding pyrimidinone analogs 3-2 by heating with aqueous HBr. Alternatively, the pyrimidinone analogs can be synthesized via the N-oxide intermediates 4-2 as shown in Scheme 4. Scheme 5 shows the N-alkylation of the pyrimidinone-pyrole 3-2 to arrive at the compounds of Formula I. Other electrophilic reagents can be employed to alkylate or acylate the nitrogen, as will be apparent to the skilled artisan.

SCHEME 1

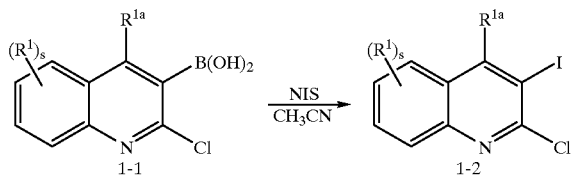

-continued
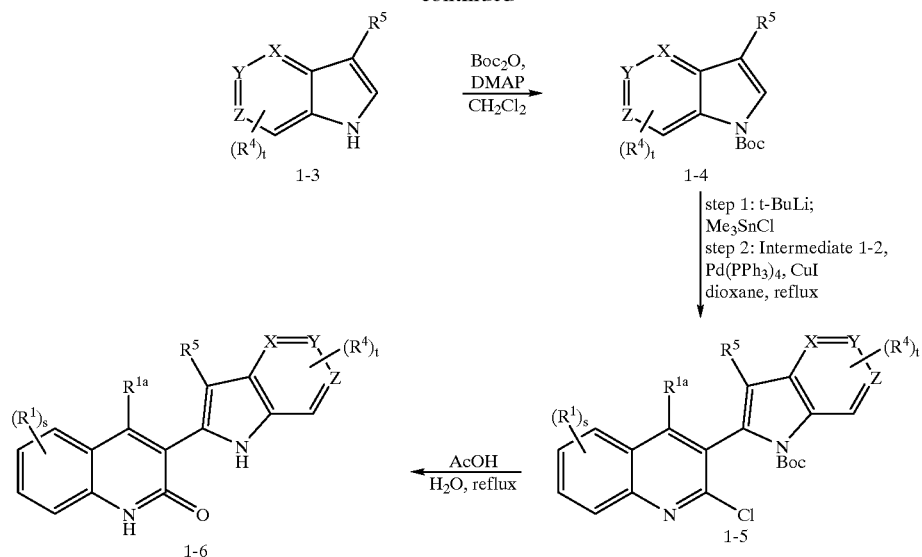
SCHEME 2
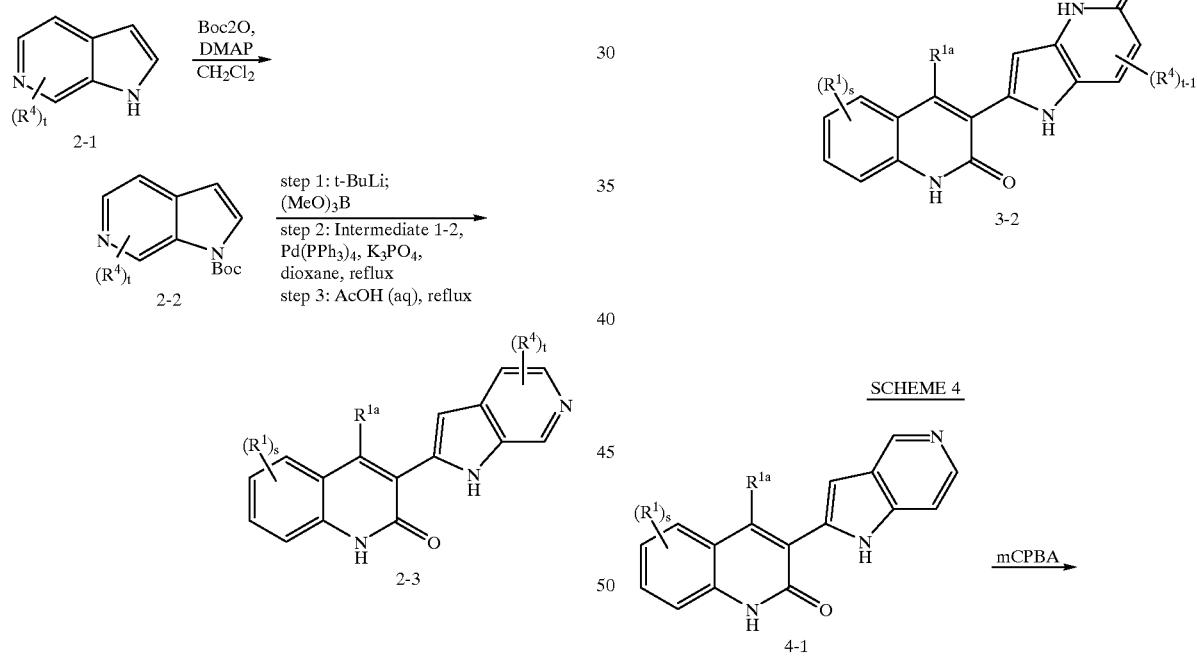
SCHEME 3
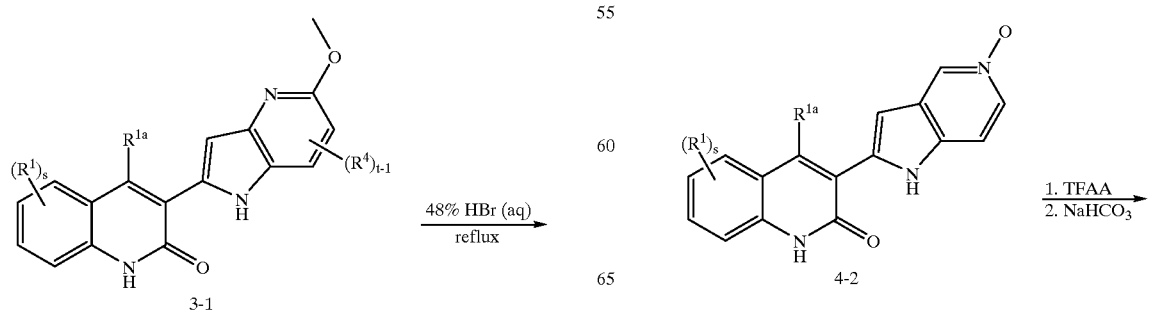
SCHEME 4

-continued

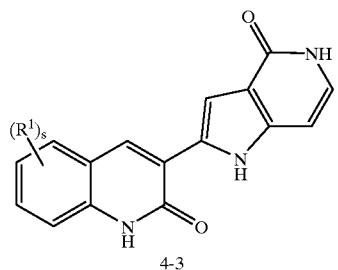

4-3

SCHEME 5

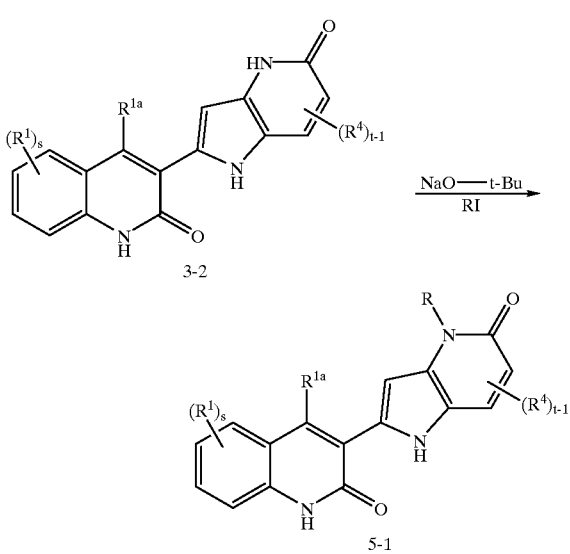

Utility

The instant compounds are useful as pharmaceutical agents for mammals, especially for humans, in the treatment of tyrosine kinase dependent diseases. Such diseases include the proliferation of tumor cells, the pathologic neovascularization (or angiogenesis) that supports solid tumor growth, ocular neovascularization (diabetic retinopathy, age-related macular degeneration, and the like) and inflammation (psoriasis, rheumatoid arthritis, and the like).

The compounds of the instant invention may be administered to patients for use in the treatment of cancer. The instant compounds inhibit tumor angiogenesis, thereby affecting the growth of tumors (J. Rak et al. Cancer Research, 55:4575–4580, 1995). The anti-angiogenesis properties of the instant compounds are also useful in the treatment of certain forms of blindness related to retinal vascularization.

The disclosed compounds are also useful in the treatment of certain bone-related pathologies, such as osteosarcoma, osteoarthritis, and rickets, also known as oncogenic osteomalacia. (Hasegawa et al., Skeletal Radiol., 28, pp.41–45, 1999; Gerber et al., Nature Medicine, Vol. 5, No. 6, pp.623–628, June 1999). And since VEGF directly promotes osteoclastic bone resorption through KDR/Flk-1 expressed in mature osteoclasts (FEBS Let. 473:161–164 (2000); Endocrinology, 141:1667 (2000)), the instant compounds are also useful to treat and prevent conditions related to bone resorption, such as osteoporosis and Paget's disease.

The claimed compounds can also be used to reduce or prevent tissue damage which occurs after cerebral ischemic events, such as stroke, by reducing cerebral edema, tissue damage, and reperfusion injury following ischemia. (Drug News Perspect 11:265–270 (1998); J. Clin. Invest. 104:1613–1620 (1999)).

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, in the case of bone-related disorders, combinations that would be useful include those with antiresorptive bisphosphonates, such as alendronate and risedronate; integrin blockers (defined further below), such as $\alpha_v\beta_3$ antagonists; conjugated estrogens used in hormone replacement therapy, such as PREMPRO®, PREMARIN® and ENDOMETRION®; selective estrogen receptor modulators (SERMs), such as raloxifene, droloxifene, CP-336,156 (Pfizer) and lasofoxifene; cathespin K inhibitors; and ATP proton pump inhibitors.

The instant compounds are also useful in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors. The instant compounds are particularly useful when coadminsitered with radiation therapy. The synergistic effects of inhibiting VEGF in combination with radiation therapy have been described in the art. (see WO 00/61186).

"Estrogen receptor modulators" refers to compounds which interfere or inhibit the binding of estrogen to the receptor, regardless of mechanism. Examples of estrogen receptor modulators include, but are not limited to, tamoxifen, raloxifene, idoxifene, LY353381, LY117081 , toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, N-4-carboxyphenyl retinamide, "Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine) platinum, benzylguanine, glufosfamide, GPX100, (trans, trans, trans)-bis-mu-(hexane-1,6-diamine)-mu-[diamine-platinum(II)]bis[diamine(chloro)platinum(II)] tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl] acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)dione, lurtotecan, 7-[2-(N-isopropylamino)ethyl]-(20S) camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido [4,3-b]carbazole-1-carboxamide, asulacrine, (5a, 5aB, 8aa, 9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4': 6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl) amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2, 1-c] quinolin-7-one, and dimesna.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,820,850; 4,916,239), pravastatin (PRAVACHOL®; see U.S. Pat. Nos. 4,346,227; 4,537,859; 4,410,629; 5,030,447 and 5,180,589), fluvastatin (LESCOL®; see U.S. Pat. Nos. 5,354,772; 4,911, 165; 4,929,437; 5,189,164; 5,118,853; 5,290,946; 5,356, 896), atorvastatin (LIPITOR®; see U.S. Pat. Nos. 5,273, 995; 4,681,893; 5,489,691; 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

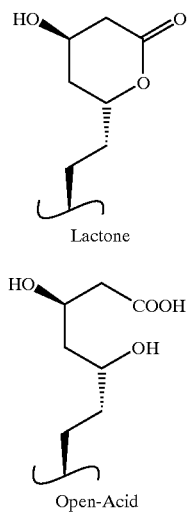

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2 (1H)-quinolinone, (–)-6-[amino(4-chlorophenyl)(1-methyl-1H-imidazol-5-yl)methyl]-4-(3-chlorophenyl)-1-methyl-2 (1H)-quinolinone, (+)-6-[amino(4-chlorophenyl)(1-methyl-1H-imidazol-5-yl)methyl]-4-(3-chlorophenyl)-1-methyl-2 (1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl)-2-piperazinone, 5(S)-n-Butyl-1-(2-methylphenyl)-4-[1-(4-cyanobenzyl)-5-imidazolylmethyl]-2-piperazinone, 1-(3-chlorophenyl) -4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl] piperidine, 4-{5-[4-Hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl) benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-Oxo-2H-[1,2'] bipyridin-5'-ylmethyl]-3H-imidazol-4-ylmethyl}benzonitrile, 4-[3-(2-Oxo-1-phenyl-1,2-dihydropyridin-4-ylmethyl)-3H-imidazol-4-ylmethyl}benzonitrile, 18,19-dihydro-19-oxo-5H,17H-6, 10:12,16-dimetheno-1H-imidazo[4,3-c][1,11,4] dioxaazacyclononadecine-9-carbonitrile, (±)-19,20-Dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacycloeicosine-9-carbonitrile, and (±)-19,20-Dihydro-3-methyl-19-oxo-5H-18,21-ethano-12,14-etheno-6,10-metheno-22H-benzo[d]imidazo[4,3-k][1,6,9, 12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp.1394–1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p.573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p.107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141–145 (1985)), and antibodies to VEGF. (see, Nature Biotechnology, Vol. 17, pp.963–968 (October 1999); Kim et al., Nature, 362, 841–844 (1993); WO 00/44777; and WO 00/61186).

As described above, the combinations with NSAID's are directed to the use of NSAID's which are potent COX-2 inhibiting agents. For purposes of this specification an NSAID is potent if it possess an $IC_{50}$ for the inhibition of COX-2 of 1 μM or less as measured by the cell or microsomal assay disclosed herein.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by the cell or micromsal assay disclosed hereinunder. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference.

Other examples of specific inhibitors of COX-2 include the following:

3-(3-fluorophenyl)-4-(4-(methylsulfonyl)phenyl)-2-(5H)-furanone;
3-(3,4-difluorophenyl)-4-(4-(methylsulfonyl)phenyl)-2-(5H)-furanone;
3-(3,4-dichlorophenyl)-4-(4-(methylsulfonyl)phenyl )-2-(5H)-furanone;
3-phenyl-4-(4-(methylsulfonyl)phenyl)-2-(5H)-furanone;
5,5-dimethyl-3-(3-fluorophenyl)-4-(methylsulfonyl)phenyl)-2-(5H)-furanone;
3-(4-methylsulfonyl)phenyl-2-phenyl-5-trifluoromethylpyridine;
2-(3-chlorophenyl)-3-(4-methylsulfonyl)phenyl-5-trifluoromethyl-pyridine;
2-(4-chlorophenyl)-3-(4-methylsulfonyl)phenyl-5-trifluoromethyl-pyridine;
2-(4-fluorophenyl)-3-(4-methylsulfonyl)phenyl-5-trifluoromethyl-pyridine;
3-(4-methylsulfonyl)phenyl-2-(3-pyridinyl)-5-trifluoromethylpyridine;
5-methyl-3-(4-methylsulfonyl)phenyl-2-phenylpyridine;
2-(4-chlorophenyl)-5-methyl-3-(4-methylsulfonyl)phenylpyridine;
5-methyl-3-(4-methylsulfonyl)phenyl-2-(3-pyridinyl)pyridine;
5-chloro-2-(4-chlorophenyl)-3-(4-methylsulfonyl)phenylpyridine;
5-chloro-3-(4-methylsulfonyl)phenyl-2-(2-pyridinyl)pyridine;
5-chloro-3-(4-methylsulfonyl)phenyl-2-(3-pyridinyl)pyridine;
5-chloro-3-(4-methylsulfonyl)phenyl-2-(4-pyridinyl)pyridine;
5-chloro-3-(4-methylsulfonyl)phenyl-2-(2-methyl-5-pyridinyl)pyridine;
2-(4-chlorophenyl)-3-(4-methylsulfonyl)phenylpyridinyl-5-carboxylic acid methyl ester;
2-(4-chlorophenyl)-3-(4-methylsulfonyl)phenylpyridinyl-5-carboxylic acid;
5-cyano-2-(4-chlorophenyl)-3-(4-methylsulfonyl)phenylpyridine;
5-chloro-3-(4-methylsulfonyl)phenyl-2-(3-pyridyl)pyridine hydromethanesulfonate;
5-chloro-3-(4-methylsulfonyl)phenyl-2-(3-pyridyl)pyridine hydrochloride;
5-chloro-3-(4-methylsulfonyl)phenyl-2-(2-methyl-5-pyridinyl)pyridine hydrochloride;
5-chloro-3-(4-methylsulfonyl)phenyl-2-(2-ethyl-5-pyridinyl)pyridine;
5-chloro-3-(4-methylsulfonyl)phenyl-2-(2-ethyl-5-pyridinyl)pyridine hydromethanesulfonate;
3-(3,4-difluorophenoxy)-5,5-dimethyl-4-(4-(methylsulfonyl)phenyl)-5H-furan-2-one;
3-(3-fluorophenoxy)-5,5-dimethyl-4-(4-(methylsulfonyl)phenyl)-5H-furan-2-one;
3-(3,5-difluorophenoxy)-5,5-dimethyl-4-(4-(methylsulfonyl)phenyl)-5H-furan-2-one;
3-phenoxy-5,5-dimethyl-4-(4-(methylsulfonyl)phenyl)-5H-furan-2-one;
3-(2,4-difluorophenoxy)-5,5-dimethyl-4-(4-(methylsulfonyl)phenyl)-5H-furan-2-one;
3-(4-chlorophenoxy)-5,5-dimethyl-4-(4-(methylsulfonyl)phenyl)-5H-furan-2-one;
3-(3,4-dichlorophenoxy)-5,5-dimethyl-4-(methylsulfonyl)phenyl)-5H-furan-2-one;

3-(4-fluorophenoxy)-5,5-dimethyl-4-(4-(methylsulfonyl)phenyl)-5H-furan-2-one;
3-(4-fluorophenylthio)-5,5-dimethyl-4-(4-(methylsulfonyl)phenyl)-5H-furan-2-one;
3-(3,5-difluorophenylthio)-5,5-dimethyl-4-(4-(methylsulfonyl)phenyl)-5H-furan-2-one;
3-phenylthio-5,5-dimethyl-4-(4-(methylsulfonyl)phenyl)-5H-furan-2-one;
3-(N-phenylamino)-5,5-dimethyl-4-(4-(methylsulfonyl)phenyl)-5H-furan-2-one;
3-(N-methyl-N-phenylamino)-5,5-dimethyl-4-(4-(methylsulfonyl)phenyl)-5H-furan-2-one;
3-cyclohexyloxy-5,5-dimethyl-4-(4-(methylsulfonyl)phenyl)-5H-furan-2-one;
3-phenylthio-4-(4-(methylsulfonyl)phenyl)-5H-furan-2-one;
3-benzyl-5,5-dimethyl-4-(4-(methylsulfonyl)phenyl)-5H-furan-2-one;
3-(3,4-difluorophenylhydroxymethyl)-5,5-dimethyl-4-(4-(methylsulfonyl)phenyl)-5H-furan-2-one;
3-(3,4-difluorobenzoyl)-5,5-dimethyl-4-(4-methylsulfonyl)phenyl)-5H-furan-2-one;
3-benzoyl-5,5-dimethyl-4-(4-(methylsulfonyl)phenyl)-5H-furan-2-one;
4-(4-(methylsulfonyl)phenyl)-3-phenoxy-1-oxaspiro[4.4]non-3-en-2-one;
4-(4-(methylsulfonyl)phenyl)-3-phenylthio-1-oxaspiro[4.4]non-3-en-2-one;
4-(2-oxo-3-phenylthio-1-oxa-spiro[4,4]non-3-en-4-yl) benzenesulfonamide;
3-(4-fluorobenzyl)-5,5-dimethyl-4-(4-(methylsulfonyl)phenyl)-5H-furan-2-one;
3-(3,4-difluorophenoxy)-5-methoxy-5-methyl-4-(4-(methylsulfonyl)phenyl)-5H-furan-2-one;
3-(5-chloro-2-pyridyloxy)-5,5-dimethyl-4-(4-(methylsulfonyl)phenyl)-5H-furan-2-one;
3-(2-pyridyloxy)-5,5-dimethyl-4-(4-(methylsulfonyl)phenyl)-5H-furan-2-one;
3-(6-methyl-2-pyridyloxy)-5,5-dimethyl-4-(4-(methylsulfonyl)phenyl)-5H-furan-2-one;
3-(3-isoquinolinoxy)-5,5-dimethyl-4-(4-(methylsulfonyl)phenyl)-5H-furan-2-one;
3-(4-(methylsulfonyl)phenyl)-2-phenoxycyclopent-2-enone;
3-(4-(methylsulfonyl)phenyl)-2-(3,4-difluorophenoxy)cyclopent-2-enone;
5,5-dimethyl-4-(4-methylsulfonylphenyl)-3-(5-bromopyridin-2-yloxy)-5H-furan-2-one;
5,5-dimethyl-4-(4-methylsulfonylphenyl)-3-(2-propoxy)-5H-furan-2-one;
2-(3,4-difluorophenoxy)-3-(4-methylsulfonylphenyl)-cyclopent-2-enone;
3-(5-benzothiophenyloxy)-5,5-dimethyl-4-(4-(methylsulfonyl)phenyl)-5H-furan-2-one;
5,5-dimethyl-4-(4-methylsulfonyl-phenyl)-3-(pyridyl-4-oxy)-5H-furan-2-one;
5,5-dimethyl-4-(4-methylsulfonyl-phenyl)-3-(pyridyl-3-oxy)-5H-furan-2-one;
3-(2-methyl-5-pyridyloxy)-5,5-dimethyl-4-(4-(methylsulfonyl)phenyl)-5H-furan-2-one;
3-(2-fluoro-4-trifluoromethyl)phenoxy-4-(4-methylsulfonyl)phenyl)-5,5-dimethyl-5H-furan-2-one;
3-(5-chloro-2-pyridylthio)-5,5-dimethyl-4-(4-methylsulfonyl)phenyl-5H-furan-2-one;
2-(3,5-difluorophenoxy)-3-(4-methylsulfonylphenyl)-cyclopent-2-enone;
3-(2-pyrimidinoxy)-5,5-dimethyl-4-(4-methylsulfonyl)phenyl-5H-furan-2-one;
3-(3-methyl-2-pyridyloxy)-5,5-dimethyl-4-(4-methylsulfonyl)phenyl-5H-furan-2-one;
3-(3-chloro-5-pyridyloxy)-5,5-dimethyl-4-(4-(methylsulfonyl)phenyl)-5H-furan-2-one;
3-(3-(1,2,5-thiadiazolyl)oxy)-4-(4-(methylsulfonyl)phenyl)-5,5-dimethyl-5H-furan-2-one;
3-(5-isoquinolinoxy)-5,5-dimethyl-4-(4-methylsulfonyl)phenyl-5H-furan-2-one;
3-(6-amino-2-pyridyloxy)-5,5-dimethyl-4-(4-(methylsulfonyl)phenyl)-5H-furan-2-one;
3-(3-chloro-4-fluoro)phenoxy-4-(methylsulfonyl)phenyl)-5,5-dimethyl-5H-furan-2-one;
3-(6-quinolinoxy)-5,5-dimethyl-4-(4-(methylsulfonyl)phenyl)-5H-furan-2-one;
3-(5-nitro-2-pyridyloxy)-5,5-dimethyl-4-(4-methylsulfonyl)phenyl-5H-furan-2-one;
3-(2-thiazolylthio)-5,5-dimethyl-4-(4-(methylsulfonyl)phenyl)-5H-furan-2-one;
3-(3-chloro-5-pyridyloxy)-5,5-dimethyl-4-(4-(methylsulfonyl)phenyl)-5H-furan-2-one;
5,5-dimethyl-4-(4-methylsulfonylphenyl)-3-(2-propoxy)-5H-furan-2-one;
3-(3-trifluoromethyl)phenoxy-4-(4-methylsulfonyl)phenyl)-5,5-dimethyl-5H-furan-2-one;
5,5-dimethyl-(4-(4-methylsulfonyl)phenyl)-3-(piperidine-1-carbonyl)-5-H-furan-2-one;
5,5-dimethyl-3-(2-Butoxy)-4-(4-methylsulfonylphenyl)-5H-furan-2-one;
5,5-dimethyl-4-(4-methylsulfonylphenyl)-3-(3-pentoxy)-5H-furan-2-one;
2-(5-chloro-2-pyridyloxy)-3-(4-methylsulfonyl)phenylcyclopent-2-enone;
3-(4-methyl-2-pyridyloxy)-5,5-dimethyl-4-(4-methylsulfonyl)phenyl-5H-furan-2-one;
(5R)-3-(3,4-difluorophenoxy)-5-ethyl-5-methyl-4-(4-methylsulfonyl)phenyl-5H-furan-2-one;
(5R)-3-(4-chlorophenoxy)-5-ethyl-5-methyl-4-(4-methylsulfonyl)phenyl-5H-furan-2-one;
3-(2-methyl-3-pyridyloxy)-5,5-dimethyl-4-(4-methylsulfonyl)phenyl-5H-furan-2-one;
3-(4-methyl-5-nitro-2-pyridyloxy)-5,5-dimethyl-4-(4-methylsulfonyl)phenyl-5H-furan-2-one;
3-(5-chloro-4-methyl-2-pyridyloxy)-5,5-dimethyl-4-(4-methylsulfonyl)phenyl-5H-furan-2-one;
3-(5-fluoro-4-methyl-2-pyridyloxy)-5,5-dimethyl-4-(4-methylsulfonyl)phenyl-5H-furan-2-one;
3-(3-chloro-2-pyridyloxy)-5,5-dimethyl-4-(4-methylsulfonyl)phenyl-5H-furan-2-one;
3-(4-fluorophenoxy)-5-methyl-4-(4-methylsulfonyl)phenyl-5-propyl-5H-furan-2-one;
3-(N,N-diethylamino)-5,5-dimethyl-4-(4-(methylsulfonyl)phenyl)-5H-furan-2-one;
5,5-dimethyl-4-(4-methylsulfonyl-phenyl)-3-(3,5-dichloro-2-pyridyloxy)-5H-furan-2-one;
(5R)-3-(4-bromophenoxy)-5-ethyl-5-methyl-4-(4-methylsulfonyl)phenyl-5H-furan-2-one;
(5R)-3-(4-methoxyphenoxy)-5-ethyl-5-methyl-4-(4-methylsulfonyl)phenyl-5H-furan-2-one;
(5R)-3-(5-chloro-2-pyridyloxy)-5-methyl-4-(4-methylsulfonyl)phenyl-5-(2,2,2-trifluoroethyl)-5H-furan-2-one;
3-(5-chloro-2-pyridyloxy)-5-methyl-4-(4-methylsulfonyl)phenyl-5-propyl-5H-furan-2-one;
3-(1-cyclopropyl-ethoxy)-5,5-dimethyl-4-(4-methylsulfonyl)phenyl)-5H-furan-2-one;
5-methyl-4-(4-(methylsulfonyl)phenyl)-3-(2-(propoxy)-5-(2-trifluoroethyl)-5H-furan-2-one;

5(R)-5-ethyl-5-methyl-4-(4-(methylsulfonyl)phenyl)-3-(2-propoxy)-5H-furan-2-one;
5,5-dimethyl-3-(2,2-dimethylpropyloxy)-4-(4-(methylsulfonyl)phenyl)-5H-furan-2-one;
5(R)-3-(1-cyclopropyl-ethoxy)-5-ethyl-5-methyl-4-(4-(methyl sulfonyl)phenyl-5H-furan-2-one;
5(S)-5-ethyl-5-methyl-4-(4-(methylsulfonyl)phenyl-3-(2-propoxy)-5H-furan-2-one.
3-(1-cyclopropylethoxy)-5,5-dimethyl-4-(4-(methylsulfonyl)phenyl)-5H-furan-2-one;
3-(1-cyclopropylethoxy)-5,5-dimethyl-4-(4-(methylsulfonyl)phenyl)-5H-furan-2-one;
5,5-dimethyl-3-(isobutoxy)-4-(4-(methylsulfonyl)phenyl)-5H-furan-2-one;
3-(4-bromophenoxy)-5,5-dimethyl-4-(4-(methylsulfonyl)phenyl)-5H-furan-2-one;
3-(2-quinolinoxy)-5,5-dimethyl-4-(4-(methylsulfonyl)phenyl)-5H-furan-2-one;
3-(2-chloro-5-pyridyloxy)-5,5-dimethyl-4-(4-(methylsulfonyl)phenyl)-5H-furan-2-one;
3-(6-benzothiazolyloxy)-5,5-dimethyl-4-(4-(methylsulfonyl)phenyl)-5H-furan-2-one;
3-(6-chloro-2-pyridyloxy)-5,5-dimethyl-4-(4-(methylsulfonyl)phenyl)-5H-furan-2-one;
3-(4-quinazolyloxy)-5,5-dimethyl-4-(4-(methylsulfonyl)phenyl)-5H-furan-2-one;
(5R)-3-(5-fluoro-2-pyridyloxy)-5-ethyl-5-methyl-4-(4-methylsulfonyl)phenyl-5H-furan-2-one;
(5R)-3-(4-fluorophenoxy)-5-ethyl-5-methyl-4-(4-methylsulfonyl)phenyl-5H-furan-2-one;
(5R)-3-(5-fluoro-2-pyridyloxy)-5-methyl-4-(4-methylsulfonyl)phenyl-5-(2,2,2-trifluoroethyl)-5H-furan-2-one;
3-(1-isoquinolinyloxy)-5,5-dimethyl-4-(methylsulfonyl)phenyl-5H-furan-2-one;
(5R)-3-(4-fluorophenoxy)-5-methyl-4-(4-methylsulfonyl)phenyl-5-(2,2,2-trifluoroethyl)-5H-furan-2-one;
3-(3-fluoro-2-pyridyloxy)-5,5-dimethyl-4-(4-methylsulfonyl)phenyl)-5H-furan-2-one;
(5R)-3-(3,4-difluorophenoxy)-5-methyl-4-(4-methylsulfonyl)phenyl-5-(2,2,2-trifluoroethyl)-5H-furan-2-one;
(5R)-3-(5-chloro-2-pyridyloxy)-5-ethyl-5-methyl-4-(4-methylsulfonyl)phenyl-5H-furan-2-one;
3-(3,4-difluorophenoxy)-5-methyl-5-trifluoromethyl-4-(4-methylsulfonyl)phenyl-5H-furan-2-one;
3-(3,4-difluorophenoxy)-5-methyl-4-(4-(methylsulfonyl)phenyl)-5-propyl-5H-furan-2-one;
3-cyclobutyloxy-5,5-dimethyl-4-(4-methylsulfonylphenyl-5H-furan-2-one;
3-(1-indanyloxy)-5,5-dimethyl-4-(4-(methylsulfonyl)phenyl)-5H-furan-2-one;
3-(2-indanyloxy)-5,5-dimethyl-4-(4-methylsulfonyl)phenyl)-5H-furan-2-one;
3-cyclopentyloxy-5,5-dimethyl-4-(4-methylsulfonylphenyl)5H-furan-2-one;
3-(3,3-dimethylcyclopentyloxy)-5,5-dimethyl-4-(4-methylsulfonyl-phenyl)-5H-furan-2-one;
3-isopropoxy-5-methyl-4-(4-methylsulfonylphenyl)-5-propyl-5H-furan-2-one;
3-(2-methoxy-5-pyridyloxy)-5,5-dimethyl-4-(4-methylsulfonyl)phenyl)-5H-furan-2-one;
3-(5-methyl-2-pyridyloxy)-5,5-dimethyl-4-(4-methylsulfonyl)phenyl)-5H-furan-2-one;
(5RS)-3-(3,4-difluorophenoxy)-5-methyl-4-(4-methylsulfonyl)phenyl-5-(2,2,2-trifluoroethyl)-5H-furan-2-one;

3-(3-chloro-4-methoxyphenoxy)-5,5-dimethyl-4-(4-methylsulfonyl)phenyl-5H-furan-2-one;
(5R)-3-(3-chloro-4-methoxyphenoxy)-5-ethyl-5-methyl-4-(4-methylsulfonyl)phenyl-5H-furan-2-one;
(5R)-3-(4-chlorophenoxy)-5-trifluoroethyl-5-methyl-4-(4-methylsulfonyl)phenyl-5H-furan-2-one;
(5R)-3-(4-bromophenoxy)-5-trifluoroethyl-5-methyl-4-(4-methylsulfonyl)phenyl-5H-furan-2-one;
5-cyclopropylmethyl-3-(3,4-difluorophenoxy)-5-methyl-(4-methylsulfonyl)phenyl-5H-furan-2-one;
(5R)-3-(3-fluorophenoxy)-5-ethyl-5-methyl-4-(4-methylsulfonyl)phenyl-5H-furan-2-one;
(5R)-3-(4-chloro-3-fluorophenoxy)-5-ethyl-5-methyl-4-(4-methylsulfonyl)phenyl-5H-furan-2-one;
(5R)-3-phenoxy-5-ethyl-5-methyl-4-(4-methylsulfonyl)phenyl-5H-furan-2-one;
(5R)-3-(4-chloro-3-methylphenoxy)-5-ethyl-5-methyl-4-(4-methylsulfonyl)phenyl-5H-furan-2-one;
3-(4-chloro-3-methylphenoxy)-5-5-dimethyl-4-(4-methylsulfonyl)phenyl-5H-furan-2-one;
(5R)-3-(5-bromo-2-pyridyloxy)-4-(4-methylsulfonylphenyl)-5-methyl-5-(2,2,2-trifluoroethyl)-5H-furan-2-one;
(5R)-3-(5-bromo-2-pyridyloxy)-4-(4-methylsulfonylphenyl)-5-ethyl-5-methyl-5H-furan-2-one;
3-(5-chloro-6-methyl-2-pyridyloxy)-5,5-dimethyl-4-(4-methylsulfonyl)phenyl-5H-furan-2-one;
3-(5-cyclopropyl-2-pyridyloxy)-5,5-dimethyl-4-(4-methylsulfonyl)phenyl-5H-furan-2-one;
3-(1-cyclopropylethoxy)-4-(4-methylsulfonyl)phenyl-5H-furan-2-one; and
3-(cyclopropylmethoxy)-4-(4-methylsulfonyl)phenyl-5H-furan-2-one;

or a pharmaceutically acceptable salt or stereoisomer thereof.

Inhibitors of COX-2 that are particularly useful in the instant method of treatment are:

3-phenyl-4-(4-(methylsulfonyl)phenyl)-2-(5H)-furanone; and

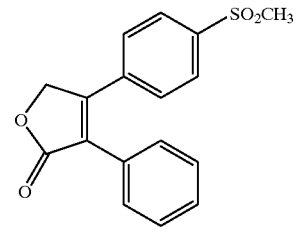

5-chloro-3-(4-methylsulfonyl)phenyl-2-(2-methyl-5-pyridinyl)pyridine;

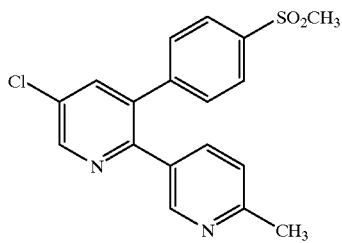

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

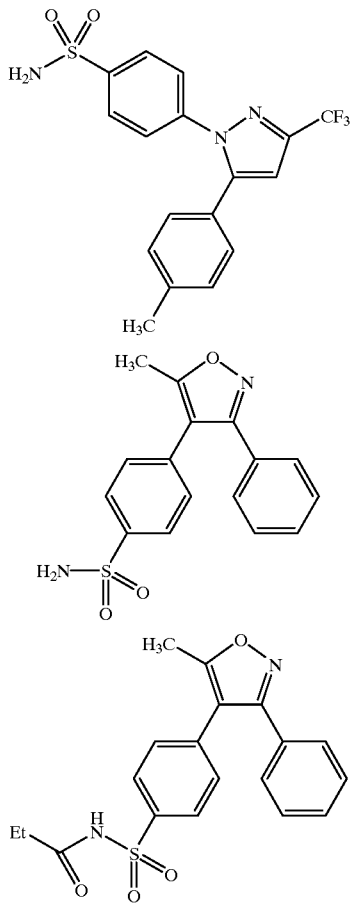

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998.

Other examples of angiogenesis inhibitors include, but are not limited to, endostation, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide,CM101, squalamine, combretastatin, RPI4610, NX31838, sulfated mannopentaose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI157, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

The instant compounds are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, *Platelets* 10, 285–292, 1999). Therefore, the present compounds can serve to inhibit metastasis, alone or in combination with GP IIb/IIIa) antagonists. Examples of other fibrinogen receptor antagonists include abciximab, eptifibatide, sibrafiban, lamifiban, lotrafiban, cromofiban, and CT50352.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

ASSAYS

The compounds of the instant invention described in the Examples were tested by the assays described below and were found to have kinase inhibitory activity. Other assays are known in the literature and could be readily performed by those of skill in the art. (see, for example, Dhanabal et al., *Cancer Res.* 59:189–197; Xin et al., *J. Biol. Chem.* 274:9116–9121; Sheu et al., *Anticancer Res.* 18:4435–4441; Ausprunk et al., *Dev. Biol.* 38:237–248; Gimbrone et al., *J. Natl. Cancer Inst.* 52:413–427; Nicosia et al., *In Vitro* 18:538–549).

VEGF Receptor Kinase Assay

VEGF receptor kinase activity is measured by incorporation of radio-labeled phosphate into polyglutamic acid, tyrosine, 4:1 (pEY) substrate. The phosphorylated pEY product is trapped onto a filter membrane and the incorporation of radio-labeled phosphate quantified by scintillation counting.

MATERIALS

VEGF Receptor Kinase

The intracellular tyrosine kinase domains of human KDR (Terman, B. I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in Spodoptera frugiperda (Sf21) insect cells (Invitrogen) using a baculovirus expression vector (pAcG2T, Pharmingen).

Lysis Buffer 50 mM Tris pH 7.4, 0.5 M NaCl, 5 mM DTT, 1 mM EDTA, 0.5% triton X-100, 10% glycerol, 10 mg/mL of each leupeptin, pepstatin and aprotinin and 1 mM phenylmethylsulfonyl fluoride (all Sigma).

Wash Buffer 50 mM Tris pH 7.4, 0.5 M NaCl, 5 mM DTT, 1 mM EDTA, 0.05% triton X-100, 10% glycerol, 10 mg/mL of each leupeptin, pepstatin and aprotinin and 1 mM phenylmethylsulfonyl fluoride.

Dialysis Buffer 50 mM Tris pH 7.4, 0.5 M NaCl, 5 mM DTT, 1 mM EDTA, 0.05% triton X-100, 50% glycerol, 10 mg/mL of each leupeptin, pepstatin and aprotinin and 1 mM phenylmethylsuflonyl fluoride.

10×Reaction Buffer 200 mM Tris, pH 7.4, 1.0 M NaCl, 50 mM $MnCl_2$, 10 mM DTT and 5 mg/mL bovine serum albumin (Sigma).

Enzyme Dilution Buffer 50 mM Tris, pH 7.4, 0.1 M NaCl, 1 mM DTT, 10% glycerol, 100 mg/mL BSA.

10×Substrate

750 µg/mL poly (glutamic acid, tyrosine; 4:1) (Sigma).

Stop Solution

30% trichloroacetic acid, 0.2 M sodium pyrophosphate (both Fisher).

Wash Solution

15% trichloroacetic acid, 0.2 M sodium pyrophosphate.

Filter Plates

Millipore #MAFC NOB, GF/C glass fiber 96 well plate.

Method

A. Protein Purification

1. Sf21 cells were infected with recombinant virus at a multiplicity of infection of 5 virus particles/cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 100,000×g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1. Add 5 μl of inhibitor or control to the assay in 50% DMSO.
2. Add 35 μl of reaction mix containing 5 μl of 10×reaction buffer, 5 μl 25 mM ATP/10 μCi [$^{33}$P]ATP (Amersham), and 5 μl 10×substrate.
3. Start the reaction by the addition of 10 μl of KDR (25 nM) in enzyme dilution buffer.
4. Mix and incubate at room temperature for 15 minutes.
5. Stop by the addition of 50 μl stop solution.
6. Incubate for 15 minutes at 4° C.
7. Transfer a 90 μl aliquot to filter plate.
8. Aspirate and wash 3 times with wash solution.
9. Add 30 μl of scintillation cocktail, seal plate and count in a Wallac Microbeta scintillation counter.

Human Umbilical Vein Endothelial Cell Mitogenesis Assay

Expression of VEGF receptors that mediate mitogenic responses to the growth factor is largely restricted to vascular endothelial cells. Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^{3}$H]thymidine into cellular DNA.

Materials

HUVECs

HUVECs frozen as plimary culture isolates are obtained from Clonetics Corp. Cells are maintained in Endothelial Growth Medium (EGM; Clonetics) and are used for mitogenic assays at passages 3–7.

Culture Plates

NUNCLON 96-well polystyrene tissue culture plates (NUNC #167008).

Assay Medium

Dulbecco's modification of Eagle's medium containing 1 g/mL glucose (low-glucose DMEM; Mediatech) plus 10% (v/v) fetal bovine serum (Clonetics).

Test Compounds

Working stocks of test compounds are diluted serially in 100% dimethylsulfoxide (DMSO) to 400-fold greater than their desired final concentrations. Final dilutions to 1× concentration are made directly into Assay Medium immediately prior to addition to cells.

10×Growth Factors

Solutions of human VEGF$_{165}$ (500 ng/mL; R&D Systems) and bFGF (10 ng/mL; R&D Systems) are prepared in Assay Medium.

10× [$^{3}$H]Thymidine

[Methyl-$^{3}$H]Thymidine (20 Ci/mmol; Dupont-NEN) is diluted to 80 uCi/mL in low-glucose DMEM.

Cell Wash Medium

Hank's balanced salt solution (Mediatech) containing 1 mg/mL bovine serum albumin (Boehringer-Mannheim).

Cell Lysis Solution

1 N NaOH, 2% (w/v) Na$_2$CO$_3$.

Method

1. HUVEC monolayers maintained in EGM are harvested by trypsinization and plated at a density of 4000 cells per 100 μL Assay Medium per well in 96-well plates. Cells are growth-arrested for 24 hours at 37° C. in a humidified atmosphere containing 5% CO$_2$.
2. Growth-arrest medium is replaced by 100 μL Assay Medium containing either vehicle (0.25% [v/v] DMSO) or the desired final concentration of test compound. All determinations are performed in triplicate. Cells are then incubated at 37° C./5% CO$_2$ for 2 hours to allow test compounds to enter cells.
3. After the 2-hour pretreatment period, cells are stimulated by addition of 10 μL/well of either Assay Medium, 10×VEGF solution or 10×bFGF solution. Cells are then incubated at 37° C./5% CO$_2$.
4. After 24 hours in the presence of growth factors, 10× [$^{3}$H] Thymidine (10 μL/well) is added.
5. Three days after addition of [$^{3}$H]thymidine, medium is removed by aspiration, and cells are washed twice with Cell Wash Medium (400 μL/well followed by 200 μL/well). The washed, adherent cells are then solubilized by addition of Cell Lysis Solution (100 μL/well) and warming to 37° C. for 30 minutes. Cell lysates are transferred to 7-mL glass scintillation vials containing 150 μL of water. Scintillation cocktail (5 mL/vial) is added, and cell-associated radioactivity is determined by liquid scintillation spectroscopy.

Based upon the foregoing assays the compounds of formula I are inhibitors of VEGF and thus are useful for the inhibition of angiogenesis, such as in the treatment of ocular disease, e.g., diabetic retinopathy and in the treatment of cancers, e.g., solid tumors. The instant compounds inhibit VEGF-stimulated mitogenesis of human vascular endothelial cells in culture with IC$_{50}$ values between 0.01–5.0 μM. These compounds also show selectivity over related tyrosine kinases (e.g., FGFR1 and the Src family; for relationship between Src kinases and VEGFR kinases, see Eliceiri et al., Molecular Cell, Vol. 4, pp.915–924, December 1999).

EXAMPLES

Examples provided are intended to assist in a further understanding of the invention. Particular materials employed, species and conditions are intended to be further illustrative of the invention and not limiting of the reasonable scope thereof.

Example 1

3-(5-methoxy-1H-pyrrolo[3,2-b]pyridin-2-yl)-1H-quinolin-2-one

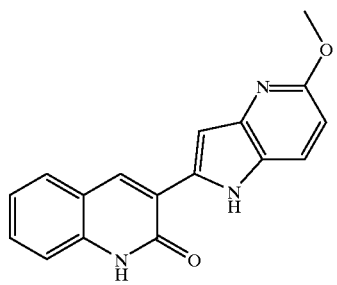

Step 1: Synthesis of 2-chloro-3-iodo-quinoline (Intermediate A)

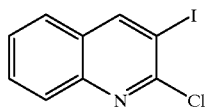

A suspension of 3-(2-chloro)-quinolineboronic acid (5.05 g, 24.3 mmol, 1 equiv, prepared by the method of Marsais, F; Godard, A.; Queguiner, G. *J. Heterocyclic Chem.* 1989, 26, 1589–1594) and N-iodosuccinimide (5.48 g, 24.4 mmol, 1.00 equiv) in acetonitrile (300 mL) was stirred at 23° C. in the dark for 20 hours. The reaction mixture was concentrated to dryness, and the resulting yellow solid was partitioned between saturated aqueous sodium bicarbonate solution and dichloromethane. The organic layer was washed with water, then dried over magnesium sulfate and concentrated to give 2-chloro-3-iodo-quinoline (intermediate A) as a pale yellow solid.

$^1$H NMR (400 MHz, CDCl$_3$) δ8.67 (s, 1H), 7.99 (br d, 1H, J=8.4 Hz), 7.75 (br t, 1H, J=7.7 Hz), 7.72 (br d, 1H, J=7.8 Hz), 7.57 (br t, 1H, J=7.6 Hz).

Step 2: Synthesis of Intermediate B

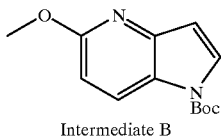

Intermediate B

A solution of 5-methoxy-1H-pyrrolo[3,2-b]pyridine (0.930 g, 6.28 mmol, 1 equiv, prepared by the method of Mazeas, D.; Guillaumet, G.; Viaud, M-C *Heterocycles* 1999, 50, 1065–1080), di-tert-butyl dicarbonate (1.64 g, 4.05 mmol, 1.20 equiv), and 4-dimethylaminopyiidine (10 mg, 0.082 mmol, 0.013 equiv) in dichloromethane (30 mL) was stirred at 23° C. for 1 hour. The reaction mixture was concentrated, and the residue was purified by flash column chromatography (100% hexanes initially, grading to 30% ethyl acetate in hexanes) to afford intermediate B as a colorless oil.

$^1$H NMR (300 MHz, CDCl$_3$) δ8.24 (br d, 1H, J=9.0 Hz), 7.72 (br d, 1H, J=3.4 Hz), 6.69 (d, 1H, J=9.0 Hz), 6.63 (d, 1H, J=3.9 Hz), 3.99 (s, 3H), 1.67 (s, 9H).

Step 3: Synthesis of Intermediate C

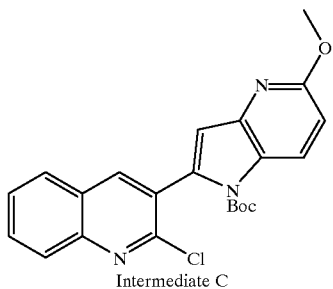

Intermediate C

Step 1: A solution of tert-butyllithium in pentane (1.7 M, 3.95 mL, 6.72 mmol, 1.20 equiv) was added to a solution of intermediate B (1.39 g, 5.60 mmol, 1 equiv) in THF (70 mL) at −78° C. The orange solution was stirred for 15 min, then a solution of trimethyltin chloride (2.23 g, 11.2 mmol, 2.00 equiv) in THF (4.0 mL) was added. The reaction mixture was warmed to 23° C., then partitioned between aqueous pH 7 phosphate buffer and a 1:1 mixture of ethyl acetate and hexane (100 mL). The organic layer was dried over sodium sulfate and concentrated.

Step 2: A deoxygenated solution of this residue, intermediate A (0.800 g, 2.76 mmol, 0.500 equiv), tetrakis (triphenylphosphine)palladium (0.160 g, 0.140 mmol, 0.025 equiv), and cuprous iodide (0.053 g, 0.28 mmol, 0.05 equiv) in dioxane (40 mL) was heated at 90° C. for 20 hours. The reaction mixture was cooled, then partitioned between brine (150 mL) and ethyl acetate (150 mL). The organic layer was dried over sodium sulfate, then concentrated. The residue was purified by flash column chromatography (100% hexanes initially, grading to 30% ethyl acetate in hexanes) to afford intermediate C as a light yellow foam.

$^1$H NMR (300 MHz, CDCl$_3$) δ8.44 (d, 1H, J=9.2 Hz), 8.18 (s, 1H), 8.08 (d, 1H, J=8.5 Hz), 7.88 (d, 1H, J=8.2 Hz), 7.79 (ddd, 1H, J=8.5, 7.0, 1.5 Hz), 7.63 (ddd, 1H, J=8.5, 7.0, 1.5 Hz), 6.78 (d, 1H, J=8.8 Hz), 6.72 (s, 1H), 4.02 (s, 3H), 1.27 (s, 9H).

Step 4: Synthesis of 3-(5-methoxy-1H-pyrrolo[3,2-b]pyridin-2-yl)-1H-quinolin-2-one A solution of intermediate C (900 mg, 2.20 mmol) was heated in a 1:1 mixture of acetic acid and water (50 mL) at reflux for 16 hours. The reaction mixture was concentrated, and the residue was partitioned between aqueous saturated sodium bicarbonate solution (150 mL) and hot ethyl acetate (3×200 mL). The combined organic layers were dried over sodium sulfate and concentrated. The residue was suspended in ethyl ether (200 mL), filtered, then air-dried to give the titled compound as a yellow solid.

$^1$H NMR (300 MHz, (CD$_3$)$_2$SO) δ12.23 (s, 1H), 11.75 (s, 1H), 8.58 (s, 1H), 786 (br d, 1H, J=9.2 Hz), 7.75 (br d, 1H, J=7.6, Hz), 7.54 (br t, 1H, J=7.8 Hz), 7.39 (d, 1H, J=8.2 Hz), 7.26 (br t, 1H, J=7.6 Hz), 7.18 (br s, 1H), 6.57 (d, 1H, J=8.5 Hz), 3.88 (s, 3H). HRMS (electrospray FT/ICR) calcd for C17H14N3O2 [M+H]$^+$ 292.1081, found 292.1059.

Examples 2–4 were synthesized in analogous fashion to Example 1 starting from the corresponding azaindoles prepared by the method of Hands, D.; Bishop, B.; Cameron, M.; Edwards, J. S.; Cottrell, I. F.; Wright, S. H. B *Synthesis* 1996, 887–882.

Example 2

3-(5-methoxy-1H-pyrrolo[2,3-c]pyridin-2-yl)-1H-quinolin-2-one

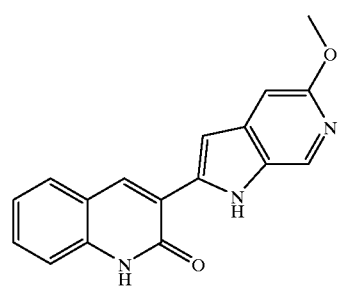

Step 1: Synthesis of Intermediate D

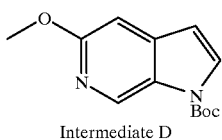

Intermediate D

A solution of 5-methoxy-1H-pyrrolo[2,3-c]pyridine (190 mg, 1.28 mmol, 1 equiv, prepared by the method of Mazeas, D.; Guillaumet, G.; Viaud, M-C *Heterocycles* 1999, 50, 1065–1080), di-tert-butyl dicarbonate (336 mg, 1.54 mmol, 1.20 equiv), and 4-dimethylaminopyridine (10 mg, 0.082 mmol, 0.064 equiv) in dichloromethane (20 mL) was stirred at 23° C. for 2 hours. The reaction mixture was concentrated, and the residue was purified by flash column chromatography (100% hexanes initially, grading to 20% ethyl acetate in hexanes) to afford intermediate E as a colorless oil which solidified upon standing (180 mg, 56%).

$^1$H NMR (300 MHz, CDCl$_3$) δ8.89 (br s, 1H), 7.70 (br d, 1H, J=4.0 Hz), 6.86 (s, 1H), 6.48 (d, 1H, J=3.9 Hz), 3.98 (s, 3H), 1.68 (s, 9H).

Step 2: Synthesis of 3-(5-methoxy-1H-pyrrolo[2,3-c]pyridin-2-yl)-1H-quinolin-2-one Step 1: A solution of tert-butyllithium in pentane (1.7 M, 0.45 mL, 0.77 mmol, 1.20 equiv) was added to a solution of intermediate D (160 mg, 0.644 mmol, 1 equiv) in THF (15 mL) at −78° C. The bright-yellow solution was stirred for 10 min, then trimethylborate (0.144 mL, 1.29 mmol, 2.00 equiv) was added. The reaction mixture was warmed to 0° C., then partitioned between aqueous half-saturated ammonium chloride solution and ethyl acetate (2×75 mL). The organic layer was dried over sodium sulfate and concentrated to give a white solid (160 mg).

Step 2: A deoxygenated solution of this solid, intermediate A (150 mg, 0.51 mmol, 1.0 equiv), tetrakis(triphenylphosphine)palladium (30 mg, 0.026 mmol, 0.05 equiv), and potassium phosphate (327 mg, 1.54 mmol, 3.00 equiv) in dioxane (15 mL) was heated at reflux for 20 hours. The reaction mixture was cooled, then partitioned between water (75 mL) and ethyl acetate (2×75 mL). The organic layer was dried over sodium sulfate, then concentrated. The residue was passed through a column of flash-grade silica gel (40% EtOAc in hexanes initially, grading to 100% EtOAc). The fractions containing primarily the desired coupled product were concentrated.

Step 3: A solution of this residue in a 1:1 mixture of acetic acid and water was heated at reflux for 20 hours. The reaction mixture was concentrated, and the residue was purified by reverse-phase column chromatography (5% acetonitrile in water initially, grading to 100% acetonitrile). The desired fractions were concentrated, and the residue was partitioned between saturated aqueous sodium bicarbonate solution and ethyl acetate. The organic layer was dried over sodium sulfate and concentrated to afford the titled compound as a yellow solid.

$^1$H NMR (400 MHz, (CD$_3$)$_2$SO) δ12.22 (s, 1H), 12.00 (s, 1H), 8.62 (s, 1H), 8.49 (s, 1H), 7.74 (br d, 1H, J=7.7 Hz), 7.53 (br t, 1H, J=7.7 Hz), 7.37 (br d, 1H, J=8.2 Hz), 7.23 (br t, 1H, J=7.5 Hz), 7.12 (s, 1H), 6.84 (s, 1H), 3.84 (s, 3H). HRMS (electrospray FT/ICR) calcd for C17H14N3O2 [M+H]$^+$ 292.1081, found 292.1068.

Example 3

3-(5-oxo-4,5-dihydro-1H-pyrrolo[3,2-b]pyridin-2-yl)-1H-quinolin-2-one

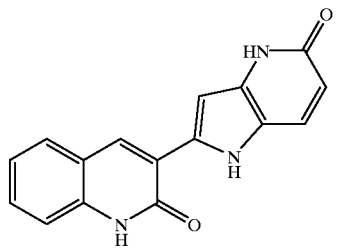

A solution of the product from Example 1 (100 mg, 0.343 mmol) in aqueous 48% HBr solution was heated at reflux for 20 hours. The reaction mixture was cooled and the yellow solid which had precipitated was filtered and washed with aqueous 1 N hydrochloric acid solution. The filtered solid was then dried under vacuum to afford the titled product as a yellow solid.

$^1$H NMR (300 MHz, (CD$_3$)$_2$SO) δ14.20 (br s, 1H), 12.51 (s, 1H), 12.40 (s, 1H), 8.81 (s, 1H), 8.29 (br d, 1H, J=9.2 Hz), 7.81 (br d, 1H, J=7.9 Hz), 7.60 (br t, 1H, J=7.0 Hz), 7.41 (d, 1H, J=8.2 Hz), 7.30 (br t, 1H, J=7.6 Hz), 7.14 (br s, 1H), 6.70 (d, 1H, J=8.8 Hz).

Example 4

3-(5-oxo-5,6-dihydro-1H-pyrrolo[2,3-c]pyridin-2-yl)-1H-quinolin-2-one

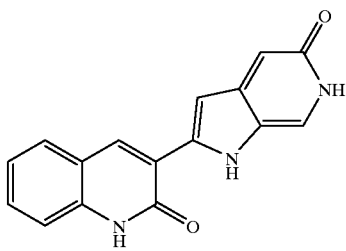

The titled compound can be made by the reaction of the corresponding methyl ether with HBr according to the procedure in Example 3 above.

Example 5

3-(4-oxo-4,5-dihydro-1H-pyrrolo[3,2-c]pyridin-2-yl)-1H-quinolin-2-one

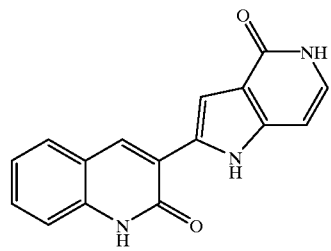

The titled compound can be made via oxidation of the product from Example 3 followed by rearrangement (see Scheme 4).

Example 6

3-(4-methyl-5-oxo-4,5-dihydro-1H-pyrrolo[3,2-b]pyridin-2-yl)-1H-quinolin-2-one

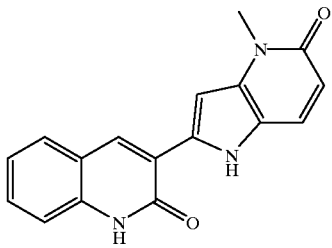

Sodium tert-butoxide (10 mg, 0.11 mmol, 1.0 equiv) and iodomethane (13 µL, 0.22 mmol, 2.0 equiv) were added sequentially to a suspension of the product from Example 3 (30 mg, 0.11 mmol, 1 equiv) in THF (10 mL) at 23° C. The reaction mixture was stirred for 20 hours. Additional sodium tert-butoxide (20 mg, 0.22 mmol, 2.0 equiv) and iodomethane (26 µL, 0.44 mmol, 4.0 equiv) were added in 2 equal portions over 1 hour, and then the reaction mixture was allowed to stir an additional 1 hour. Water (5 mL) was added, and the resulting mixture was concentrated to a volume of 2 mL. The mixture was purified by reverse phase HPLC to afford the titled compound as a yellow solid.

$^1$H NMR (300 MHz, (CD$_3$)$_2$SO) δ12.28 (s, 1H), 11.94 (s, 1H), 8.56 (s, 1H), 7.78 (d, 1H, J=9.5 Hz), 7.73 (br d, 1H, J=7.9 Hz), 7.53 (br t, 1H, J=7.0 Hz), 7.38 (br d, 1H, J=8.2 Hz), 7.26 (br t, 1H, J=7.3 Hz), 7.03 (br d, J=1.5 Hz), 6.18 (d, 1H, J=9.2 Hz).

Examples 7–9 were synthesized in analogous fashion to Example 1 starting from the corresponding azaindoles prepared by the method of Hands, D.; Bishop, B.; Cameron, M.; Edwards, J. S.; Cottrell, I. F.; Wright, S. H. B *Synthesis* 1996, 887–882. The products can be converted to the N-alkylated compounds of Formula I via the procedure in Scheme 4 followed by alkylation as in Scheme 5, or by other procedures readily available in the chemical literature.

Example 7

3-(1H-pyrrolo[2,3-c]pyridin-2-yl)-1H-quinolin-2-one

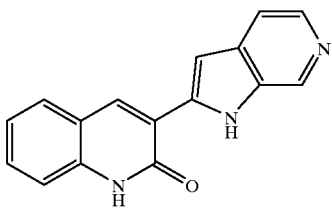

$^1$H NMR (400 MHz, (CD$_3$)$_2$SO) δ12.26 (s, 1H), 12.03 (s, 1H), 8.89 (br s, 1H), 8.70 (br s, 1H), 8.09 (br d, 1H, J=5.0 Hz), 7.78 (br d, 1H, J=7.7 Hz), 7.57 (br t, 1H, J=8.0 Hz), 7.53 (br d, 1H, J=5.3 Hz), 7.40 (br d, 1H, J=8.3 Hz), 7.31 (br s, 1H), 7.28 (br t, 1H, J=7.6 Hz).

Example 8

3-(1H-pyrrolo[3,2-c]pyridin-2-yl)-1H-quinolin-2-one

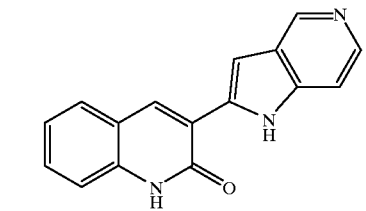

$^1$H NMR (400 MHz, (CD$_3$)$_2$SO) δ12.23 (s, 1H), 11.97 (s, 1H), 8.87 (br s, 1H), 8.61 (s, 1H), 8.18 (br s, 1H), 7.75 (br d, 1H, J=7.7 Hz), 7.55 (br t, 1H, J=8.0 Hz), 7.50 (br s, 1H), 7.45 (br s, 1H), 7.39 (br d, 1H, J=8.2 Hz), 7.27 (br t, 1H, J=7.6 Hz).

Example 9

3-(1H-pyrrolo[3,2-b]pyridin-2-yl)-1H-quinolin-2-one

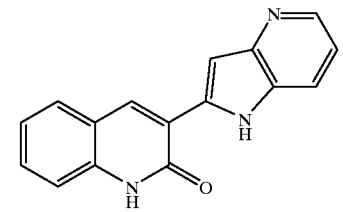

$^1$H NMR (400 MHz, (CD3OD) δ8.62 (s, 1H), 8.31 (dd, 1H, J=4.7, 1.3 Hz), 7.92 (br d, 1H, J=8.2 Hz), 7.81 (br d, 1H, J=7.8 Hz), 7.58 (br t, 1H, J=7.6 Hz), 7.40 (br d, 1H, J=8.0 Hz), 7.34 (br s, 1H), 7.31 (br t, 1H, J=8.0 Hz), 7.18 (dd, 1H, J=8.2, 4.7 Hz). HRMS (electrospray FT/ICR) calcd for C16H11N3O [M+H]$^+$ 262.0975, found 262.0975.

What is claimed is:
1. A compound of Formula I

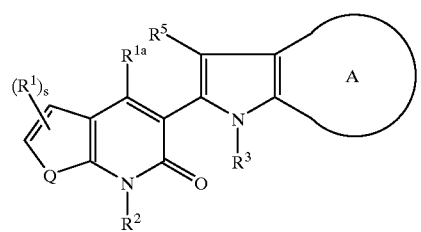

or a pharmaceutically acceptable salt or stereoisomer thereof, wherein

Q is S, O, or —E=D—;

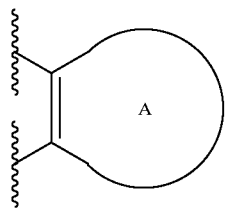

is selected from the following:

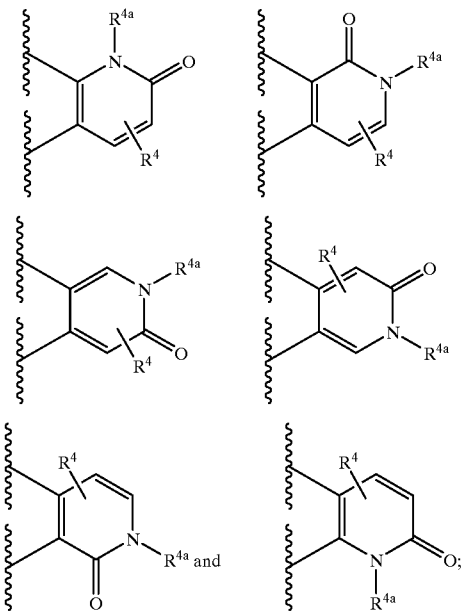

a is 0 or 1;
b is 0 or 1;
s is 1 or 2;
m is 0, 1, or 2;
E=D is C=N, N=C, or C=C;
$R^1$, $R^{1a}$, $R^4$ and $R^5$ are independently selected from:
1) H,
2) $(C=O)_aO_bC_1-C_{10}$ alkyl, optionally substituted with one to three substituents selected from $R^6$,
3) $(C=O)_aO_b$aryl, optionally substituted with one to three substituents selected from $R^6$,
4) $(C=O)_aO_bC_2-C_{10}$ alkenyl, optionally substituted with one to three substituents selected from $R^6$,
5) $(C=O)_aO_bC_2-C_{10}$ alkynyl, optionally substituted with one to three substituents selected from $R^6$,
6) $SO_mC_1-C_{10}$ alkyl, optionally substituted with one to three substituents selected from $R^6$,
7) $SO_m$aryl, optionally substituted with one to three substituents selected from $R^6$,
8) $CO_2H$,
9) halo,
10) CN,
11) OH,
12) $O_bC_1-C_6$ perfluoroalkyl, and
13) $(C=O)_aNR^7R^8$;
$R^2$ and $R^3$ are independently selected from the group consisting of:
1) H,
2) $(C=O)O_aC_1-C_{10}$ alkyl,
3) $(C=O)O_a$aryl,
4) $C_1-C_{10}$ alkyl,
5) $SO_mC_1-C_{10}$ alkyl,
6) $SO_m$aryl,
7) $(C=O)_aO_bC_2-C_{10}$ alkenyl,
8) $(C=O)_aO_bC_2-C_{10}$ alkynyl, and
9) aryl,
said alkyl, aryl, alkenyl and alkynyl is optionally substituted with one to three substituents selected from $R^6$;
$R^{4a}$ is selected from the group consisting of:
1) $(C=O)O_aC_1-C_{10}$ alkyl,
2) $(C=O)O_a$aryl,
3) $C_1-C_{10}$ alkyl,
4) $SO_mC_1-C_{10}$ alkyl,
5) $SO_m$aryl,
6) $(C=O)_aO_bC_2-C_{10}$ alkenyl,
7) $(C=O)_aO_bC_2-C_{10}$ alkynyl, and
8) aryl,
said alkyl, aryl, alkenyl and alkynyl is optionally substituted with one to three substituents selected from $R^6$;
$R^6$ is:
1) H,
2) $(C=O)_aO_bC_1-C_6$ alkyl,
3) $(C=O)_aO_b$aryl, optionally substituted with one to three substituents selected from $R^{6a}$,
4) $C_2-C_{10}$ alkenyl,
5) $C_2-C_{10}$ alkynyl,
6) heterocyclyl, optionally substituted with one to three substituents selected from $R^{6a}$,
7) $CO_2H$,
8) halo,
9) CN,
10) OH,
11) oxo,
12) $O_bC_1-C_6$ perfluoroalkyl, or
13) $NR^7R^8$;
$R^{6a}$ is:
1) H,
2) $SO_m$aryl,
3) $SO_mC_1-C_6$ alkyl,
4) $(C=O)_aO_bC_1-C_6$ alkyl,
5) $(C=O)_aO_b$aryl,
6) $C_2-C_{10}$ alkenyl,
7) $C_2-C_{10}$ alkynyl,
8) heterocyclyl,
9) $CO_2H$,
10) halo,
11) CN,
12) OH,
13) oxo,
14) $O_bC_1-C_6$ perfluoroalkyl, or
15) $N(C_1-C_6 \text{ alkyl})_2$;
$R^7$ and $R^8$ are independently selected from:
1) H,
2) $(C=O)O_bC_1-C_{10}$ alkyl, optionally substituted with one to three substituents selected from $R^{6a}$,
3) $(C=O)O_b$aryl, optionally substituted with one to three substituents selected from $R^{6a}$,
4) $C_1-C_{10}$ alkyl, optionally substituted with one to three substituents selected from $R^{6a}$,
5) aryl, optionally substituted with one to three substituents selected from $R^{6a}$,
6) $C_2-C_{10}$ alkenyl, optionally substituted with one to three substituents selected from $R^{6a}$,
7) $C_2-C_{10}$ alkynyl, optionally substituted with one to three substituents selected from $R_{6a}$, and 8) heterocyclyl, or $R^7$ and $R^8$ can be taken together with the nitrogen to which they are attached to form a 5–7 membered heterocycle containing, in addition to the nitrogen, one or two additional heteroatoms selected from N, O and S, said heterocycle optionally substituted with one to three substituents selected from $R^{6a}$.

2. The compound of claim 1, wherein Q is E=D.
3. The compound of claim 2, wherein E=D is C=C.
4. The compound of claim 3, wherein $R^1$, $R^{1a}$, $R^4$ and $R^5$ are independently selected from:
  1) H,
  2) $(C=O)_aO_bC_1$–$C_6$ alkyl, optionally substituted with one to three substituents selected from $R^6$,
  3) $(C=O)_aO_b$aryl, optionally substituted with one to three substituents selected from $R^6$,
  4) $(C=O)_aO_bC_2$–$C_6$ alkenyl, optionally substituted with one to three substituents selected from $R^6$,
  5) $CO_2H$,
  6) halo,
  7) CN,
  8) OH,
  9) $O_bC_1$–$C_3$ perfluoroalkyl, and
  10) $(C=O)_aNR^7R^8$;

$R^2$ and $R^3$ are independently selected from the group consisting of:
  1) H,
  2) $(C=O)O_aC_1$–$C_6$ alkyl, and
  3) $C_1$–$C_6$ alkyl;

$R^{4a}$ is $(C=O)O_aC_1$–$C_6$ alkyl or $C_1$–$C_6$ alkyl;

$R^6$ is:
  1) H,
  2) $(C=O)_aO_bC_1$–$C_6$ alkyl,
  3) $(C=O)_aO_b$aryl, optionally substituted with one to three substituents selected from $R^{6a}$,
  4) $C_2$–$C_6$ alkenyl,
  5) heterocyclyl, optionally substituted with one to three substituents selected from $R^{6a}$,
  6) $CO_2H$,
  7) halo,
  8) CN,
  9) OH,
  10) oxo,
  11) $O_bC_1$–$C_3$ perfluoroalkyl, or
  12) $NR^7R^8$;

$R^{6a}$ is:
  1) H,
  2) $SO_m$aryl,
  3) $SO_mC_1$–$C_6$ alkyl,
  4) $(C=O)_aO_bC_1$–$C_6$ alkyl,
  5) $(C=O)_aO_b$aryl,
  6) $C_2$–$C_6$ alkenyl,
  7) heterocyclyl,
  8) $CO_2H$,
  9) halo,
  10) CN,
  11) OH,
  12) oxo,
  13) $O_bC_1$–$C_3$ perfluoroalkyl, or
  14) $N(C_1$–$C_6$ alkyl)$_2$;

$R^7$ and $R^8$ are independently selected from:
  1) H,
  2) $(C=O)O_bC_1$–$C_6$ alkyl, optionally substituted with one to three substituents selected from $R^{6a}$,
  3) $(C=O)O_b$aryl, optionally substituted with one to three substituents selected from $R^{6a}$,
  4) $C_1$–$C_6$ alkyl, optionally substituted with one to three substituents selected from $R^{6a}$,
  5) aryl, optionally substituted with one to three substituents selected from $R^{6a}$,
  6) $C_2$–$C_6$ alkenyl, optionally substituted with one to three substituents selected from $R^{6a}$, and
  7) heterocyclyl, or $R^7$ and $R^8$ can be taken together with the nitrogen to which they are attached to form a 5–7 membered heterocycle containing, in addition to the nitrogen, one or two additional heteroatoms selected from N, O and S, said heterocycle optionally substituted with one to three substituents selected from $R^{6a}$.

5. The compound of claim 3, wherein a is 0 or 1;

b is 0 or 1;

s is 1;

$R^1$ and $R^4$ are independently selected from:
  1) H,
  2) $(C=O)_aO_bC_1$–$C_6$ alkyl, optionally substituted with one to three substituents selected from $R^6$,
  3) $(C=O)_aO_b$aryl, optionally substituted with one to three substituents selected from $R^6$,
  4) $(C=O)_aO_bC_2$–$C_6$ alkenyl, optionally substituted with one to three substituents selected from $R^6$,
  5) $(C=O)_aO_bC_2$–$C_6$ alkynyl, optionally substituted with one to three substituents selected from $R^6$,
  6) $CO_2H$,
  7) halo,
  8) CN,
  9) OH,
  10) $O_bC_1$–$C_3$ perfluoroalkyl, and
  11) $(C=O)_aNR^7R^8$;

$R^2$ and $R^3$ are independently selected from H and methyl;

$R^{4a}$ is methyl;

$R^5$ and $R^{1a}$ are H;

$R^6$ is:
  1) H,
  2) $(C=O)_aO_bC_1$–$C_6$ alkyl,=O)$_aO_b$aryl, optionally substituted with one to three substituents selected from $R^{6a}$,$C_2$–$C_{10}$ alkenyl,
  3) $C_2$–$C_{10}$ alkynyl,
  4) heterocyclyl, optionally substituted with one to three substituents selected from $R^{6a}$,
  5) $CO_2H$,
  6) halo,
  7) CN,
  8) OH,
  9) oxo,
  10) $O_bC_1$–$C_3$ perfluoroalkyl, or
  11) $NR^7R^8$;

$R^{6a}$ is:
  1) H,
  2) $SO_m$aryl,
  3) $SO_mC_1$–$C_6$ alkyl,
  4) $(C=O)_aO_bC_1$–$C_6$ alky,
  5) $(C=O)_aO_b$aryl,
  6) $C_2$–$C_{10}$ alkenyl,
  7) $C_2$–$C_{10}$ alkynyl,
  8) heterocyclyl,
  9) $CO_2H$,
  10) halo,
  11) CN,
  12) OH, 13) oxo,
14) $O_bC_1-C_3$ perfluoroalkyl, or
15) $N(C_1-C_6 \text{ alkyl})_2$;

$R^7$ and $R^8$ are independently selected from:
1) H,
2) $(C=O)O_bC_1-C_6$ alkyl, optionally substituted with one to three substituents selected from $R^{6a}$,
3) $(C=O)O_b$aryl, optionally substituted with one to three substituents selected from $R^{6a}$,
4) $C_1-C_{10}$ alkyl, optionally substituted with one to three substituents selected from $R^{6a}$,
5) aryl, optionally substituted with one to three substituents selected from $R^{6a}$,
6) $C_2-C_6$ alkenyl, optionally substituted with one to three substituents selected from $R^{6a}$,
7) $C_2-C_6$ alkynyl, optionally substituted with one to three substituents selected from $R^{6a}$, and
8) heterocyclyl, or $R^7$ and $R^8$ can be taken together with the nitrogen to which they are attached to form a piperidinyl, piperazinyl, morpholinyl or pyrrolidinyl group, optionally substituted with one or two substituents selected from $R^{6a}$.

6. A compound which is 3-(4-methyl-5-oxo-4,5-dihydro-1H-pyrrolo[3,2-b]pyridin-2-yl)-1H-quinolin-2-one or a pharmaceutically acceptable salt or stereoisomer thereof.

7. A pharmaceutical composition which is comprised of a compound in accordance with claim 1 and a pharmaceutically acceptable carrier.

8. A method of treating cancer in a mammal in need of such treatment which is comprised of administering to said mammal a therapeutically effective amount of a compound of claim 1.

9. A method of treating cancer in accordance with claim 8 wherein the cancer is selected from cancers of the brain, genitourinary tract, lymphatic system, stomach, larynx and lung.

10. A method of treating cancer in accordance with claim 8 wherein the cancer is selected from histiocytic lymphoma, lung adenocarcinoma, small cell lung cancers, pancreatic cancer, gioblastomas and breast carcinoma.

11. A method of treating or preventing a disease in which angiogenesis is implicated, which is comprised of administering to a mammal in need of such treatment a therapeutically effective amount of a compound of claim 1.

12. A method in accordance with claim 11 wherein the disease is an ocular disease.

13. A method of treating or preventing retinal vascularization which is comprised of administering to a mammal in need of such treatment a therapeutically effective amount of compound of claim 1.

14. A method of treating or preventing diabetic retinopathy which is comprised of administering to a mammal in need of such treatment a therapeutically effective amount of compound of claim 1.

15. A method of treating or preventing age-related macular degeneration which is comprised of administering to a mammal in need of such treatment a therapeutically effective amount of a compound of claim 1.

16. A method of treating or preventing inflammatory diseases which comprises administering to a mammal in need of such treatment a therapeutically effective amount of a compound of claim 1.

17. A method according to claim 16 wherein the inflammatory disease is selected from rheumatoid arthritis, psoriasis, contact dermatitis and delayed hypersensitivity reactions.

18. A method of treating or preventing a tyrosine kinase-dependent disease or condition which comprises administering a therapeutically effective amount of a compound of claim 1.

19. A pharmaceutical composition made by combining the compound of claim 1 and a pharmaceutically acceptable carrier.

20. A process for making a pharmaceutical composition which comprises combining a compound of claim 1 with a pharmaceutically acceptable carrier.

21. A method of treating or preventing bone associated pathologies selected from osteosarcoma, osteoarthritis, and rickets which comprises administering a therapeutically effective amount of a compound of claim 1.

22. The composition of claim 7 further comprising a second compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

23. The composition of claim 22, wherein the second compound is another angiogenesis inhibitor selected from the group consisting of a tyrosine kinase inhibitor, an inhibitor of epidermal-derived growth factor, an inhibitor of fibroblast-derived growth factor, an inhibitor of platelet derived growth factor, an MMP inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, and an antibody to VEGF.

24. The composition of claim 22, wherein the second compound is an estrogen receptor modulator selected from tamoxifen and raloxifene.

25. A method of treating cancer which comprises administering a therapeutically effective amount of a compound of claim 1 in combination with radiation therapy.

26. A method of treating cancer which comprises administering a therapeutically effective amount of a compound of claim 1 in combination with a compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

27. A method of treating cancer which comprises administering a therapeutically effective amount of a compound of claim 1 in combination with radiation therapy and a compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor, 9) a reverse transcriptase inhibitor, and 10) another angiogenesis inhibitor.

28. A method of treating cancer which comprises administering a therapeutically effective amount of a compound of claim 1 and paclitaxel or trastuzumab.

29. A method of treating cancer which comprises administering a therapeutically effective amount of a compound of claim 1 and a GPIIb/IIIa antagonist.

30. The method of claim 29 wherein the GPIIb/IIIa antagonist is tirofiban.

31. A method of reducing or preventing tissue damage following a cerebral ischemic event which comprises administering a therapeutically effective amount of a compound of claim 1.

32. A method of treating or preventing cancer which comprises administering a therapeutically effective amount of a compound of claim 1 in combination with a COX-2 inhibitor.

* * * * *

UNITED STATES PATENT AND TRADEMARK OFFICE
CERTIFICATE OF CORRECTION

PATENT NO. : 6,313,138 B1
DATED : November 6, 2001
INVENTOR(S) : Mark E. Fraley, George D. Hartman and Randall W. Hartman It is certified that error appears in the above-identified patent and that said Letters Patent is hereby corrected as shown below:

<u>Column 42,</u>
Line 65, should read as follows: -- three substituents selected from $R^{6a}$, and --.

<u>Column 44,</u>
Line 59, should read as follows: -- 4) $(C=O)_a O_b C_1$-$C_6$ alkyl, --.

Signed and Sealed this

Eleventh Day of June, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,313,138 B1
DATED : November 6, 2001
INVENTOR(S) : Mark E. Fraley, George D. Hartman and Randall W. Hartman It is certified that error appears in the above-identified patent and that said Letters Patent is hereby corrected as shown below:

<u>Title page,</u>
Item [75], should read as follows:

-- Inventors: Mark E. Fraley, North Wales;
  George D. Hartman, Lansdale, both of PA (US);
  Randall W. Hungate, Newbury Park, CA (US) --

Signed and Sealed this

Twentieth Day of August, 2002

Attest:

JAMES E. ROGAN
Attesting Officer
Director of the United States Patent and Trademark Office